US 6,695,146 B2

(12) United States Patent
Call et al.

(10) Patent No.: US 6,695,146 B2
(45) Date of Patent: *Feb. 24, 2004

(54) METHOD FOR SURFACE DEPOSITION OF CONCENTRATED AIRBORNE PARTICLES

(75) Inventors: Charles J. Call, Albuquerque, NM (US); Patrick T. Call, West Richland, WA (US); Vanessa M. Kenning, Kennewick, WA (US); Andrew Kamholz, Seattle, WA (US)

(73) Assignee: MesoSystems Technology, Inc., Kennewick, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/955,481

(22) Filed: Sep. 17, 2001

(65) Prior Publication Data

US 2002/0157993 A1 Oct. 31, 2002

Related U.S. Application Data

(63) Continuation-in-part of application No. 09/494,962, filed on Jan. 31, 2000, now Pat. No. 6,290,065, which is a continuation-in-part of application No. 09/191,980, filed on Nov. 13, 1998, now Pat. No. 6,062,392, and a continuation-in-part of application No. 09/265,620, filed on Mar. 10, 1999, now Pat. No. 6,363,800.

(51) Int. Cl.[7] .............................. B07B 7/00; B07B 13/00
(52) U.S. Cl. ........................... 209/143; 209/49; 209/58; 209/59; 73/863.22
(58) Field of Search ................................. 209/134, 135, 209/136, 137, 138, 142, 143, 49, 58, 59, 55; 95/31, 32, 33; 55/462; 73/28.04, 28.05, 863.22

(56) References Cited

U.S. PATENT DOCUMENTS

| 3,001,914 A | * | 9/1961 | Andersen .................... 435/30 |
|---|---|---|---|
| 3,901,798 A | | 8/1975 | Peterson |
| 3,922,905 A | * | 12/1975 | Roth ......................... 73/28.04 |
| 3,972,226 A | * | 8/1976 | Rountree et al. .......... 73/28.05 |
| 4,670,135 A | | 6/1987 | Marple et al. |
| 4,767,524 A | | 8/1988 | Yeh et al. |
| 4,961,966 A | * | 10/1990 | Stevens et al. ............. 427/299 |
| 5,304,125 A | * | 4/1994 | Leith ........................... 604/57 |
| 5,425,802 A | | 6/1995 | Burton et al. |
| 5,533,406 A | | 7/1996 | Geise |
| 5,776,754 A | | 7/1998 | Caldwell |
| 5,786,894 A | | 7/1998 | Shields et al. |
| 5,932,795 A | * | 8/1999 | Koutrakis et al. ......... 73/28.01 |
| 6,101,886 A | * | 8/2000 | Brenizer et al. ......... 73/863.23 |
| 6,110,247 A | | 8/2000 | Birmingham et al. |
| 6,217,636 B1 | * | 4/2001 | McFarland ................... 95/216 |
| 6,240,768 B1 | * | 6/2001 | Lemonnier ................ 73/28.05 |
| 6,284,025 B1 | * | 9/2001 | Kreisberg et al. ............ 95/267 |
| 6,435,043 B1 | * | 8/2002 | Ferguson et al. ........ 73/863.22 |

* cited by examiner

*Primary Examiner*—Donald P. Walsh
*Assistant Examiner*—Joseph C Rodriguez
(74) *Attorney, Agent, or Firm*—Ronald M. Anderson

(57) ABSTRACT

The present invention employs a virtual impactor to separate a flow of fluid into a major flow and a minor flow, such that the minor flow contains a higher concentration of particulates of a desired size. The minor flow is directed toward an archival surface, causing the particulates to impact against and be deposited on the archival surface. Over time, the archival surface and the virtual impactor are moved relative to one another such that particulates collected at different times are deposited as spaced-apart spots on different portions of the archival surface. The particulates are stored on the archival surface until analysis of the particulates is required. The archival surface can be coated with a material that enhances the deposition and retention of the particulates and can further be coated with materials that sustain the life of biological organism particulates deposited on the archival surface.

17 Claims, 14 Drawing Sheets

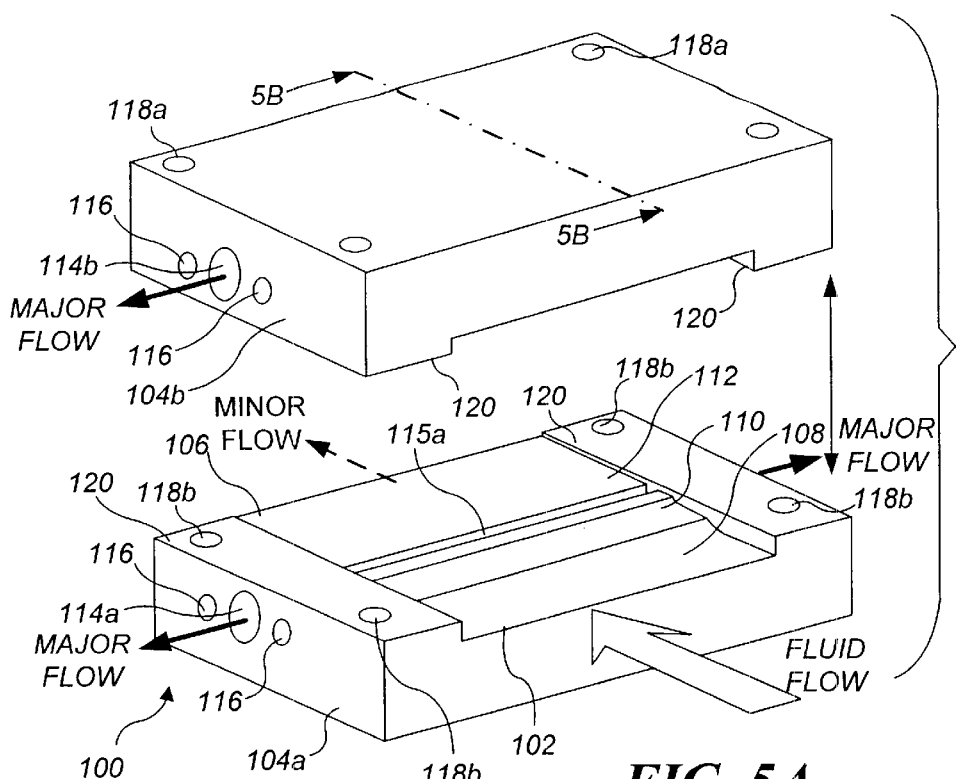
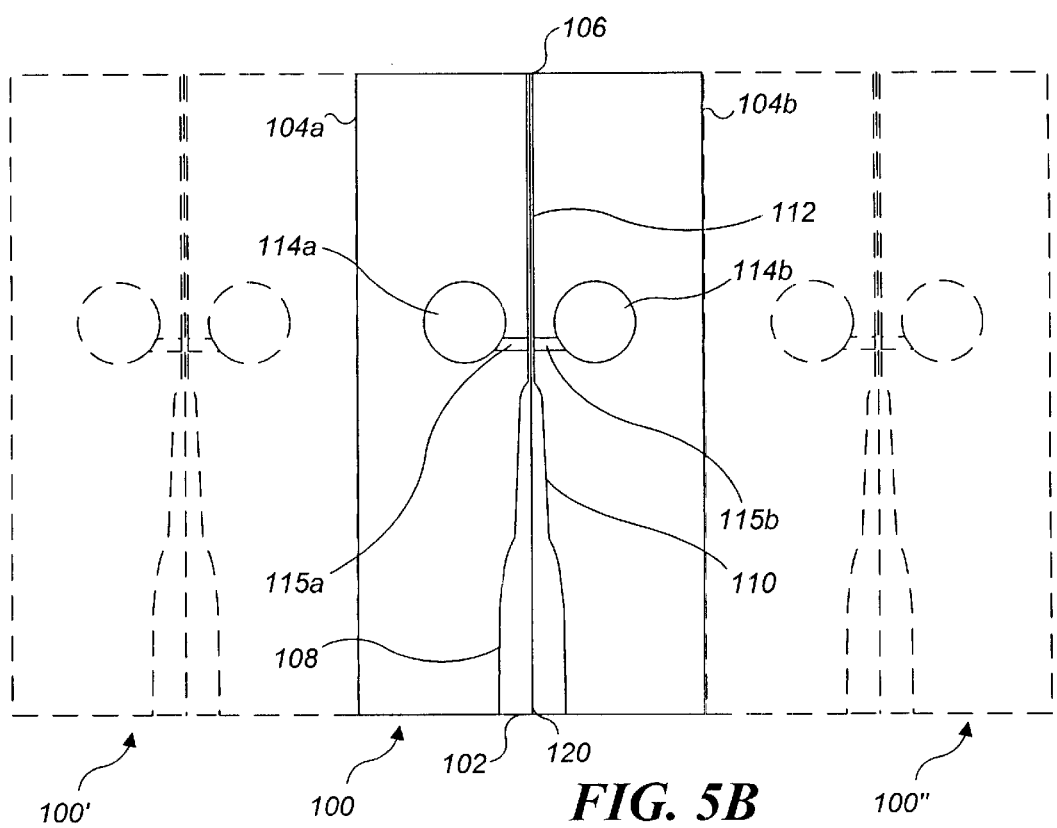

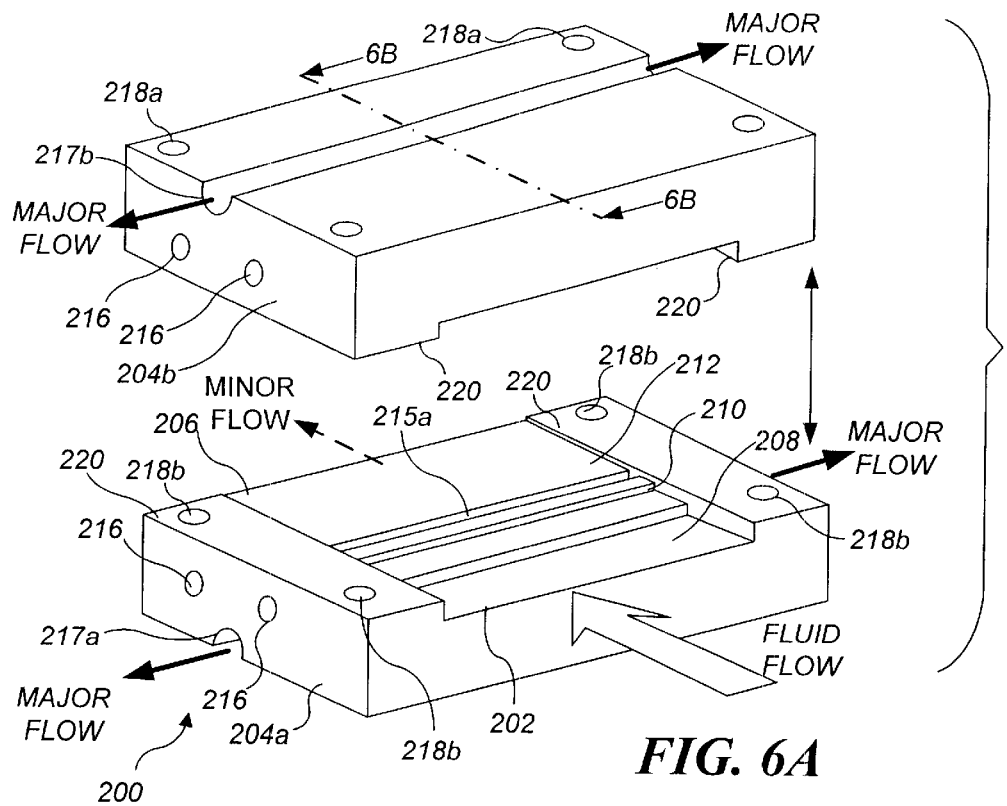
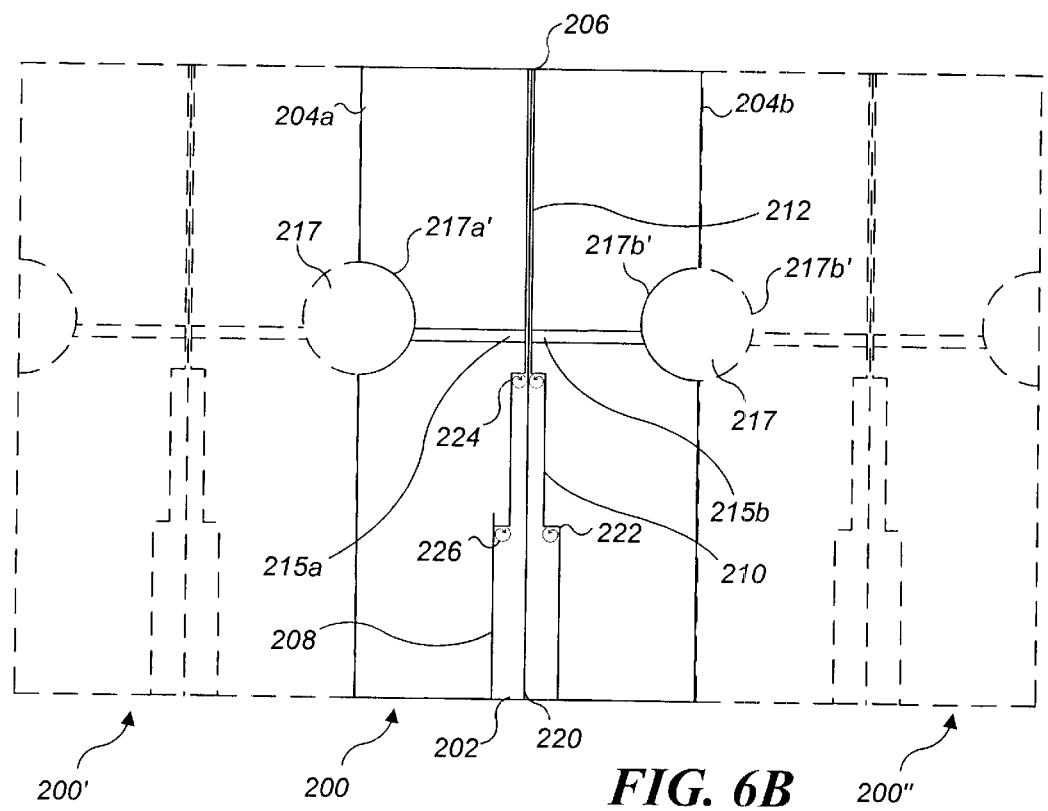
FIG. 6A
FIG. 6B

METHOD FOR SURFACE DEPOSITION OF CONCENTRATED AIRBORNE PARTICLES

RELATED APPLICATION

This application is a continuation-in-part of a utility application Ser. No. 09/494,962, filed on Jan. 31, 2000 now U.S. Pat. No. 6,290,065, which is a continuation-in-part of U.S. Pat. No. 6,062,392 (application Ser. No. 09/191,980), filed on Nov. 13, 1998, the benefit of the filing dates of which are hereby claimed under 35 U.S.C. §119(e). This application is further a continuation-in-part of prior utility application Ser. No. 09/265,620, filed on Mar. 10, 1999 now U.S. Pat. No. 6,363,800, the benefit of the filing date of which is also hereby claimed under 35 U.S.C. §119(e).

GOVERNMENT RIGHTS

This invention was made under contract with the United States Department of Defense, under Contract No. DAAM01-97-M-0006 awarded by the U.S. Department of Defense. The government has certain rights in this invention.

FIELD OF THE INVENTION

This invention generally relates to methods for collecting airborne particulates, and more specifically, to methods for collecting and archiving airborne particulates using an impact collector.

BACKGROUND OF THE INVENTION

The separation and collection of particulates/aerosols from an airstream (or other fluid streams) is of concern in several contexts. In some cases, the goal may be to simply remove the particulates/aerosols from the fluid stream, thereby cleaning or purifying the fluid. Often it is desired to remove all particulates, regardless of composition, if the particulates are above a certain size. For example, automobile painting and the fabrication of silicon chips in clean rooms represent two situations in which all particulates large enough to result in an inferior product are desirably removed from the processing environment.

In other cases, particulates are collected for analysis to determine the type and concentration of such particulates/aerosols entrained in the fluid. For example, this technology may be employed in the detection of airborne biological or chemical warfare agents, the detection of biological contamination in confined spaces, such as aircraft or hospitals, or the detection of industrial pollutants (either in ambient fluid or in the effluent of smokestacks).

Much effort has been expended in the past in the detection and classification of particulates or aerosols in fluid streams. Impactors have been used for collecting aerosol particulates for many decades. In the earliest embodiments, a stream of fluid containing the particulates was accelerated toward an impactor plate. Due to their inertia, the particulates striking the impactor plate were collected on its surface, while the fluid was deflected to the side. With these types of impactors, only larger particulates could be collected, since particulates below a certain "cut size" were carried away by the fluid stream.

However, a significant disadvantage of such an impactor is the deposition of particulates on surfaces of the impactor other than the intended collection surfaces. This phenomenon reduces the accuracy of measurement of total particulate mass concentration and of the size-fractionation of particulates, since such losses cannot be accurately estimated for aerosols or particulates of varying size, shape, or chemistry. Additionally, particulates may either become re-entrained in the fluid stream, or may bounce off the impactor's collection surface upon impact. To remedy this problem, "virtual" impactors have been developed that separate particulates from a fluid stream with techniques other than direct impaction. Virtual impactors may operate on a number of different principles, but all avoid actual "impact" as a means to separate particulates from a fluid in which the particulates are entrained and rely on differences in particulate mass to induce inertial separation. Specifically, a particulate-laden fluid stream is directed toward a surface presenting an obstruction to the forward movement of the fluid stream. The surface includes a void at the point where the particulates would normally impact the surface. When a major portion of the fluid stream changes direction to avoid the obstruction presented by the surface, fine particulates remain entrained in the deflected major portion of the fluid stream. Heavier or more dense particulates, on the other hand, fail to change direction and are collected in a region of relatively stagnant fluid (a "dead zone") that is created near the surface. The heavier particulates entrained in a minor portion of the fluid stream enter the void defined through the surface, where they can be captured or analyzed.

Some examples of virtual impactors can be found in U.S. Pat. Nos. 3,901,798; 4,670,135; 4,767,524; 5,425,802; and 5,533,406. Because typical virtual impactors do not actually collect particulates themselves, but merely redirect them into two different fluid streams according to their mass, they are essentially free of the problems of particulate bounce and particulate re-entrainment associated with actual impactor devices. Still, particulate "wall loss," i.e., unintended deposition of particulates on various surfaces of virtual impactor structures, especially at curved or bent portions, remains a challenge with some designs of virtual impactors, because typically, many stages or layers of virtual impactors are required to complete particulate separation.

An additional aspect of the collection of fluid-entrained particulates, especially with respect to particulates that will be analyzed to determine a type and concentration of particulates, relates to when the collected particulates are to be analyzed. A common practice is to sample a fluid for a period of time, and then analyze the collected sample immediately, or at least as soon as practical. Depending on the nature of the particulates for which the fluid is being sampled, immediate analysis may be required. For example, if chemical or biological agents that pose an immediate health threat are suspected, real time analysis is preferred to enable protective measures to be taken immediately, before irreversible harm can occur. However, there are also many applications, such as routine monitoring of smokestacks and waste water discharge, in which only a portion of the collected sample might need to be analyzed shortly after collection, while other portions are best archived for later analysis.

Archival samples can be prepared by taking a collected sample and manually splitting that sample into various fractions, including a first fraction to be analyzed relatively soon, and one or more additional portions to be archived for possible later analysis. While archival samples prepared by such a method are useful, the manual nature of such a method is time consuming and costly. Furthermore, during each step in which a sample is handled or manipulated (collection, separation, storage, and analysis), there is a significant chance that the sample will be inadvertently contaminated. It would thus be desirable to provide a method and apparatus that more readily enables archival samples to be prepared, with a minimal risk of contamination.

It should also be noted that the manner in which samples are collected affects the usefulness of the samples for archival purposes. Archival samples are often employed to determine more information about an event occurring at a specific time. For example, archival data collected from a smokestack might be used to determine at what time higher emissions occurred. That time could then be applied to analyze the process and equipment utilizing the smokestack to isolate the factors causing the excess emissions, so that the problem can be corrected. If the archival sample is merely a single sample collected over a 24-hour period, rather than 24 samples collected each hour for 24 hours, then little information can be obtained about when the excess emissions actually occurred, making it more difficult to determine the cause of the excess emissions. It would be therefore be desirable to provide a method and apparatus capable of providing archival samples for successive relatively short sampling periods, and which include time indexing enabling a specific archival sample to be correlated with a specific time at which the sample was taken.

Accordingly, a need exists to develop a method and apparatus capable of providing time-indexed archival samples with minimal operator effort, and minimal chance of contamination. Such archival samples desirably should include a high concentration of particulates, so that the archival samples are compact and require minimal storage space. Preferably, a virtual impactor that efficiently separates particulates from a fluid stream might be employed to collect the particulates.

SUMMARY OF THE INVENTION

The present invention is directed to a method and apparatus for concentrating, collecting, and depositing "spots" of particulates from a fluid onto a solid, archival quality medium. Such an archive, in the form of many spots collected at regular time intervals from a specific site, will enable investigation of environmental conditions (based on collected particulates) at a future time. Archived samples, each relating to a specific period of collection, can be stored and later analyzed to quantitatively and/or qualitatively test for a specific particulate at a specific time. It is anticipated that such archives will be very useful in the study of potentially hazardous particulates, including but not limited to viruses, bacteria, bio-toxins, and pathogens. Those of ordinary skill in the art will readily recognize that such archived samples can be analyzed using a variety of known analytical techniques including, but not limited to, mass spectrophotometry.

The present invention works best if fluid-entrained particulates (most often airborne particulates) are efficiently collected and concentrated, a task for which a virtual impactor, such as described in parent application Ser. No. 09/191,980, is ideal. Also, it is important to provide both a suitable archival quality surface for collecting concentrated spots of particulates to be deposited on, as well as providing means for moving the archival surface relative to the concentrated stream of particulates over time, so that spots located on different portions of the archival surface correspond to different increments of time.

Preferably the invention includes means for associating a date and time with each spot for the purpose of accurate archiving, which can be achieved in many ways including, but not limited to, a computer program that records the date and time at the instant of spot deposition, saving the data to a file for later reference. Preferably, the archival surface employed can accommodate many spots in a limited area, collected at intervals over a long period of time.

The invention is also preferably able to accept a variety of sample protocols that determine when the fluid (most often air) is sampled to produce a spot. These sample protocols, e.g., programs executed on a computing device or a hard wired logic device, can be quite simple, at times comprising only a timer that determines the waiting period between samples. Alternatively, the sample protocols can be more complex, such as protocols that comprise a schedule for sampling at variable intervals, which depend on environmental conditions determined using sensors.

The archival surface onto which the concentrated particulates are directed can be selected or modified to enhance a deposition of the particulates onto the archival surface. In some embodiments, the material of the archival surface has been selected because of its porous nature. The pore sizes are selected to be large enough to allow the fluid the particulates are entrained in to freely pass through the archival surface, and small enough to prevent the particulates themselves from passing through the archival surface. Thus the particulates are "filtered" out of the fluid stream by the archival surface. In other embodiments, the archival surface is coated with a material selected to enhance a deposition of the particulates onto the archival surface. Such surfaces generally promote adhesion via chemical attraction, (i.e. a hydrophobic-hydrophobic attraction, or a hydrophilic-hydrophilic attraction). Electrical attraction can also be employed (i.e. a positively charged surface for collecting negative particles).

In at least one embodiment, the virtual impactor includes a separation plate employed for separating a fluid stream into a major flow and a minor flow. The major flow includes a minor portion of particles that are above a predetermined size, and the minor flow includes a major portion of the particles that are above the predetermined size. The separation plate includes a block in which is defined a laterally extending passage having an inlet disposed on one edge of the block and an outlet disposed on an opposite edge of the block. This laterally extending passage has a lateral dimension that is substantially greater than a transverse dimension of the passage. Opposed surfaces of the passage between which the transverse dimension of the passage is defined generally converge toward each other within the block, so that the outlet has a substantially smaller cross-sectional area than the inlet. A transverse, laterally extending slot is defined within the block and is in fluid communication with a portion of the passage that has the substantially smaller cross-sectional area. A major flow outlet port is also defined in the block, in fluid communication with the transverse, laterally extending slot. The major flow enters the slot and exits the block through the major flow outlet port, while the minor flow exits the block through the outlet of the passage. The major flow carries the minor portion of the particles and the minor flow carries the major portion of the particles.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 5A is an isometric view of yet another alternative embodiment of a separation plate in accord with the present invention;

FIG. 5B is a cross-sectional view of the separation plate of FIG. 5A, showing additional separation plates arrayed on each side in phantom view;

FIG. 6A is an isometric view of still another alternative embodiment of a separation plate in accord with the present invention;

FIG. 6B is a cross-sectional view of the separation plate of FIG. 6A, showing additional separation plates arrayed on each side in phantom view;

DESCRIPTION OF THE PREFERRED EMBODIMENT

Overview of the Invention

Figure 1A:
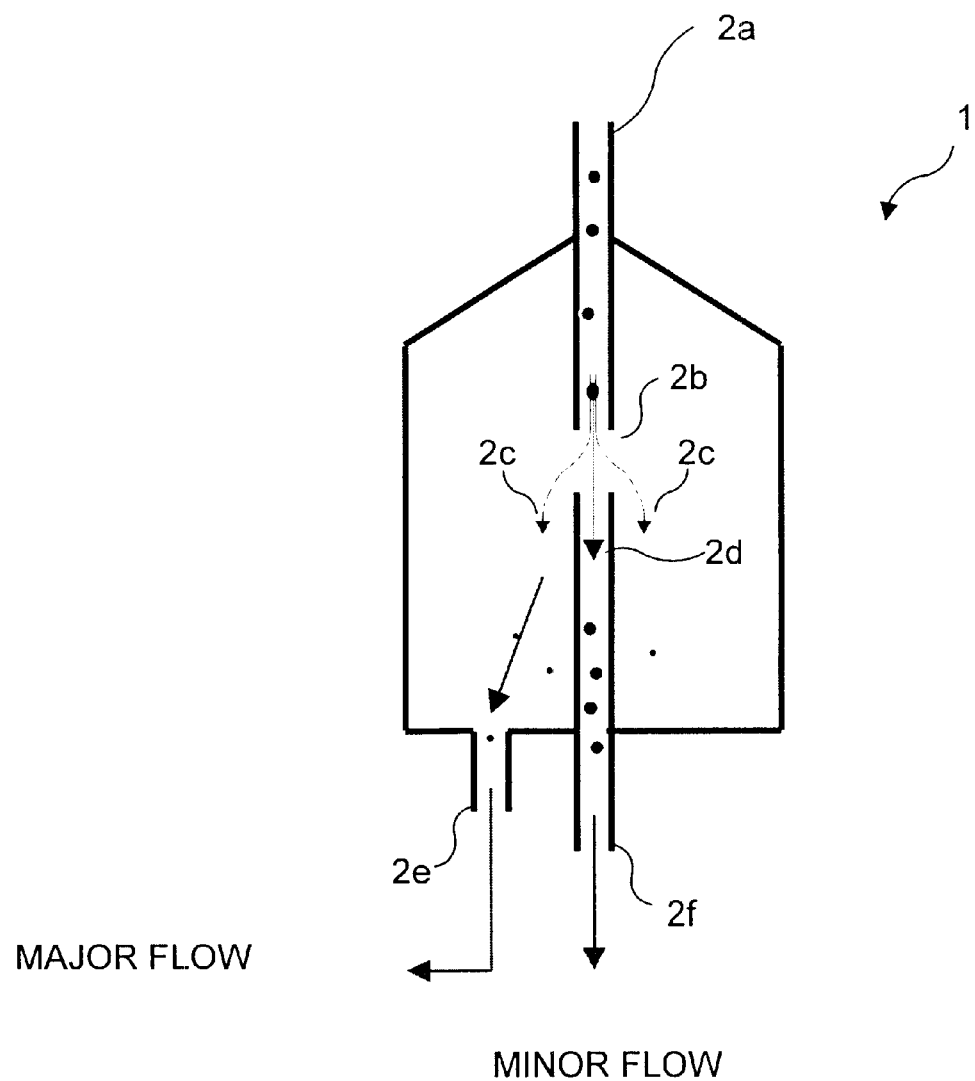
FIG. 1A is a schematic view of a virtual impactor.
Figure 1B:
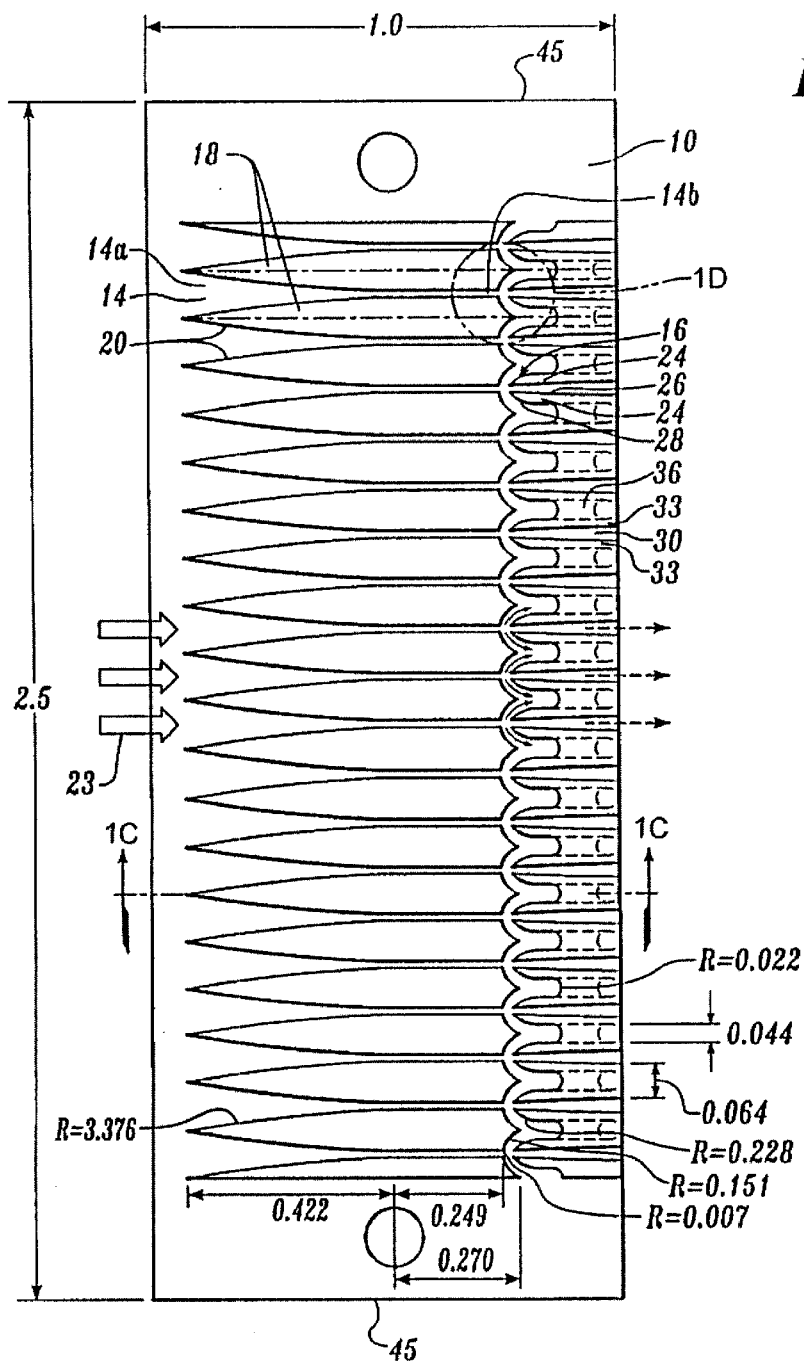
FIG. 1B is a plan view of a separation plate employed in the present invention.
Figure 1C:
FIG. 1C is a cross-sectional view of the separation plate taken along line 1C—1C of FIG. 1B.
Figure 1D:
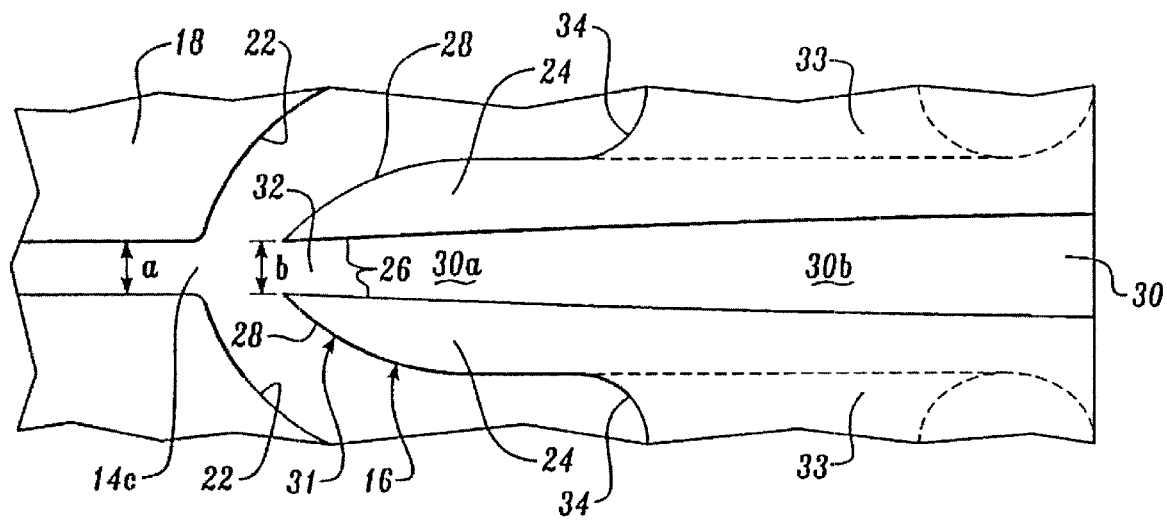
FIG. 1D is an enlarged view of a pair of a nozzle and a virtual impactor at section 1C of FIG. 1B.
Figure 1E:
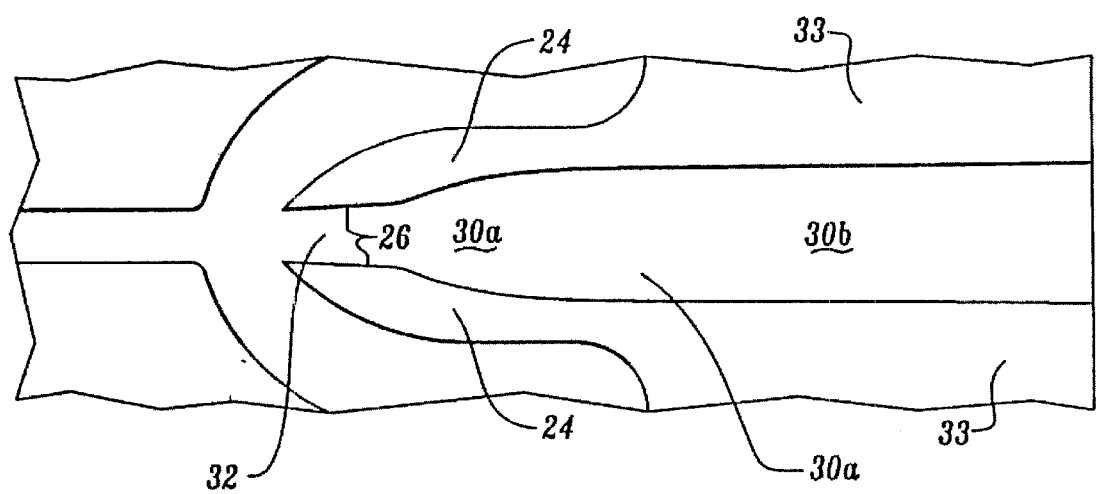
FIG. 1E is an enlarged view of another configuration of a pair of a nozzle and a virtual impactor.
Figure 2A:
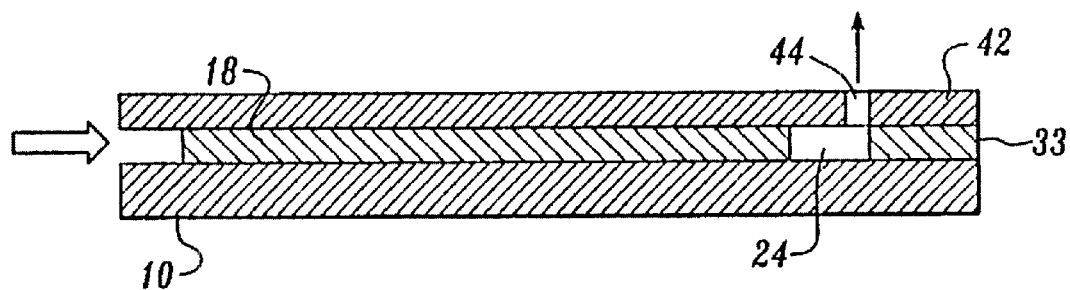
FIG. 2A is a schematic cross-sectional view of a virtual impact collector that includes another configuration of a separation plate in accord with the present invention.
Figure 2B:
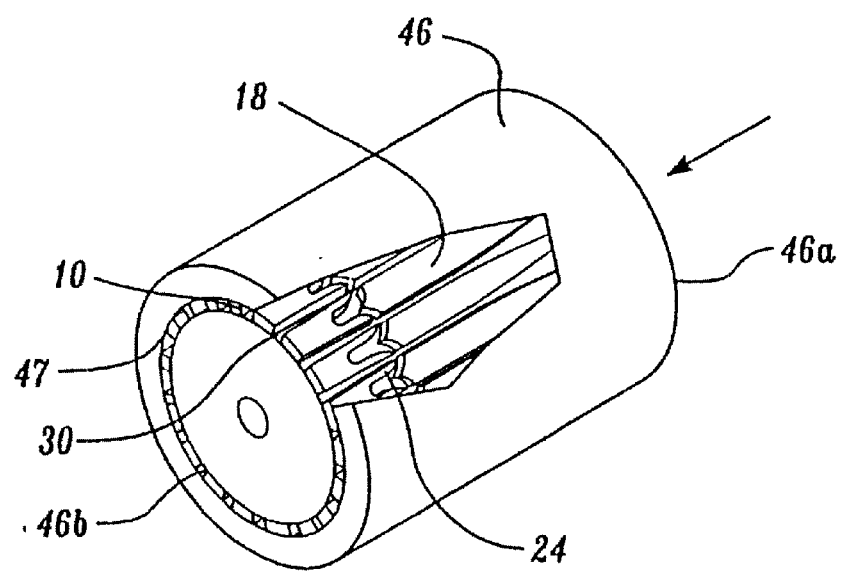
FIG. 2B is a schematic perspective view of an alternative configuration of a virtual impact collector in accord with the present invention.

The present invention involves method and apparatus for concentrating, collecting, and depositing "spots" of particulates from a fluid onto a solid, archival quality medium. Such an archive, in the form of many spots collected at known temporally spaced-apart times from a known site, will enable investigations (based on the collected particulates) of the environmental conditions at the site to be conducted at a future time. Archived particulates can include, but are not limited to, viruses, bacteria, bio-toxins, and pathogens. Those of ordinary skill in the art will readily recognize that such archived samples can be analyzed using a variety of known analytical techniques including, but not limited to, mass spectrophotometry.

The present invention employs a virtual impactor to efficiently collect and concentrate airborne particulates. The minor flow from the virtual impactor is directed towards a suitable archival quality surface to deposit concentrated spots of particulates. The archival surface is moved relative to the concentrated stream of particulates from the virtual impactor over time, so that spots or samples of the particulates that have been collected on different portions of the archival surface correspond to different times at which the particulates were collected. Preferably, the invention includes means for associating a date and time with each spot for the purpose of accurately archiving the sampled collected.

The invention also includes a control unit, such as a computing device or hard wired logic device, that executes sample protocols to determine when the fluid is sampled to produce each of the spots.

In the following description, the prefix "micro" is applied generally to components that have sub-millimeter-sized features. Micro-components are fabricated using micro-machining techniques known in the art, such as micro-milling, photolithography, deep ultraviolet (or x-ray) lithography, electro-deposition, electro-discharge machining (EDM), laser ablation, and reactive or non-reactive ion etching. It should be noted that micro-machined virtual impactors provide for increased collection efficiency and reduced pressure drops.

Also as used hereinafter, the following terms shall have the definitions set forth below:

Particulate—any separately identifiable solid, semi-solid, liquid, aerosol, or other component entrained in a fluid stream that has a greater mass than the fluid forming the fluid stream, and which is subject to separation from the fluid stream and collection for analysis. For the purposes of the present description, the mass density of particulates is assumed to be approximately 1 gm/cm$^3$. It is contemplated that the particulates may arise from sampling almost any source, including but not limited to, air, water, soil, and surfaces, and may include inorganic or organic chemicals, or living materials, e.g., bacteria, cells, or spores.

Fluid—any fluid susceptible to fluid flow, which may comprise liquids or gases, and which may entrain foreign particulates in a flow thereof. Unless otherwise noted, fluid shall mean an ambient fluid containing un-concentrated particulates that are subject to collection, not the fluid into which the particulates are concentrated after collection or capture.

Spot—an aggregate of particulates deposited upon an archival surface in a relatively small area, so that the individually small particulates are aggregated together to form a larger spot, which can be more readily observed by magnification or the naked eye.

The following description will first describe a preferred particulate collector and concentrator. Then, archival surfaces will discussed, followed by disclosure relating to apparatus for moving the archival surface relative to the collector.

Particulate Concentrating

Because particulates of interest are often present in quite small concentrations in a volume of fluid, it is highly desirable to concentrate the mass of particulates into a smaller volume of fluid. Virtual impactors can achieve such a concentration without actually removing the particulates of interest from the flow of fluid. As a result, the particulate-laden fluid flow can be passed through a series of sequentially connected virtual impactors, so that a fluid flow exiting the final virtual impactor represents a concentration of particulates 2–3 orders of magnitude greater than in the original fluid flow. The concentrated particulates can then be more readily deposited on an archival surface.

A virtual impactor uses a particle's inertia to separate it from a fluid stream that is turned, and a basic virtual impactor can be fabricated from a pair of opposing nozzles. Within a virtual impactor, the intake fluid coming through the inlet flows out from a nozzle directly at a second opposed nozzle into which only a "minor flow" is allowed to enter. This concept is schematically illustrated by a virtual impactor 1 shown in FIG. 1A. Fluid carrying entrained particulates flows through a first nozzle 2*a*. The flow from nozzle 2*a* then passes through a void 2*b* that separates nozzle 2*a* from a nozzle 2*f*. It is in void 2*b* that the flow of fluid is divided into a major flow 2*c*, which contains most of the fluid (e.g., 90%) and particles smaller than a cut (predetermined) size, and a minor flow 2*d*. Minor flow 2*d* contains a small amount of fluid (e.g., 10%) in which particulates larger than the cut size are entrained.

As a result of inertia, most of the particulates that are greater than the selected cut size are conveyed in this small minor flow and exit the virtual impactor. Most of the particulates smaller than the virtual impactor cut size are exhausted with the majority of the inlet air as the major flow. The stopping distance of a particle is an important parameter in impactor design. The cut point (size at which about 50% of the particles impact a surface, i.e., flow into the second nozzle) is related to the stopping distance. A 3 micron particle has nine times the stopping distance of a 1 micron particle of similar density.

For the present invention, several types of virtual impactors and their variants are suitable for use in collecting samples as spots for archiving purposes. Because any particular design of the minor flow nozzle can be optimized for a particular size of particles, it is contemplated that at least some embodiments of the present invention may include multiple nozzles, each with a different geometry, so that multiple particle types can be efficiently collected.

In one preferred embodiment, two virtual impactors are aligned in series, such that a concentration of particulates entrained in the minor flow of fluid exiting the second virtual impactor is approximately 100 times the original concentration.

FIGS. 1B, 1C, and 1D illustrate a first embodiment of a virtual impact separation plate 10 formed in accordance with the present invention. Separation plate 10 may be formed of various materials suitable for micro-machining, such as plastics and metals. The separation plate includes a first surface 10*a* and an opposing second surface 10*b*. The first surface 10*a* includes plural pairs of a nozzle 14 and a virtual impactor 16 (FIG. 1D). Each nozzle 14 includes an inlet end 14*a* and an outlet end 14*b* and is defined between adjacent nozzle projections 18 having a height "H" (see FIG. 1C). Two nozzle projections 18 cooperate to define one nozzle 14. Each nozzle projection 18 includes two side walls 20 that are configured to define one side of a nozzle 14, which comprise a telescoping design that generally tapers from inlet end 14*a* to outlet end 14*b*. Nozzle projection 18 further includes two generally concave walls 22 at its downstream end that are positioned to provide nozzle projection 18 with a tapered downstream "tail." In contrast to a tapered downstream tail, another of the embodiments described below that is actually more preferred includes stepped transitions that reduce the size of the passage at its outlet. Throughout the present description, the terms "upstream" and "downstream" are used to refer to the direction of a fluid stream 23 flowing through the separation plate of the present invention.

Each virtual impactor 16 comprises a pair of generally fin-shaped projections 24 having height "H." Each fin-shaped projection 24 includes an inner wall 26 and a generally convex outer wall 28. Inner walls 26 of fin-shaped projections 24 (for a pair) are spaced apart and face each other to define an upstream minor flow passage 30*a* therebetween. Convex outer walls 28 of the pair of fin-shaped projections 24 cooperatively present a generally convex surface 31 facing the fluid flow direction. Referring specifically to FIG. 1D, an inlet end 32 of upstream minor flow passage 30*a* defines a virtual impact void through convex surface 31, where "virtual" impaction occurs as more fully described below. A width of outlet end 14*b* of nozzle 14 is defined as "a," and a width of inlet end 32 of upstream minor flow passage 30*a* is defined as "b."

First surface 10*a* of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30*b* therebetween. Upstream and downstream minor flow passages 30*a* and 30*b* are aligned and communicate with each other to form minor flow passage 30. As illustrated in FIGS. 1B, 1C, and 1D, fin-shaped projections 24 of adjacent virtual impactors 16 and virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downwardly and downstream through separation plate 10 to second surfaces 10*b*. As more fully described below, orifices 34 and passageways 36 are provided merely as one example of a major flow outlet and, thus, may be replaced with any other suitable major flow outlet.

In operation, particulate-laden fluid stream 23 is caused to enter inlet ends 14*a* of nozzles 14. Nozzles 14 aerodynamically focus and accelerate particulates entrained in fluid stream 23. In this telescoping design, the aerodynamically focused fluid stream 23 exiting outlet ends 14*b* of nozzles 14 advances to convex surfaces 31 of virtual impactors 16. A major portion (at least 50%, and preferably, at least about 90%) of fluid stream 23 containing a minor portion (less than about 50%) of particulates above a certain particulate diameter size, or a cut size, hereinafter referred to as a "major flow," changes direction to avoid the obstruction presented by convex surfaces 31. Concave walls 22 of nozzle projections 18 and convex outer walls 28 of fin-shaped projections 24 cooperate to direct the major flow toward the upstream end of virtual impactor bodies 33. Bodies 33 prevent the major flow from continuing in its current direction. Orifices 34 are provided through bodies 33, so that the major flow enters orifices 34 and travels through passageways 36 to second surface 10b of separation plate 10, where it is exhausted or processed further. A minor portion (less than 50%, and preferably less than about 10%) of fluid stream 23 containing a major portion (at least about 50%) of particulates above the cut size, exits as the minor flow and is collected near a "dead" zone or a zone of nearly stagnant air created adjacent to the convex surfaces 31 of virtual impactors 16. The major portion of the particulates entrained in the minor flow "virtually" impacts the virtual impact voids at inlet ends 32 of upstream minor flow passages 30a and enters minor flow passages 30. The minor flow travels through and exits minor flow passages 30, enabling the particulates entrained therein to be collected for analysis and/or further processing.

Nozzles 14 contribute very little to particulate loss because they have a long telescoping profile, which prevents particulate deposition thereon. The long telescoping profile of the nozzles 14 also serves to align and accelerate particulates. Focusing the particulates before they enter the minor flow passage using the telescoping design may enhance the performance of the virtual impactor, since the particulates in the center of the nozzle are likely to remain entrained in the minor flow. Thus, as used herein, the term "aerodynamic focusing" refers to a geometry of a particulate separator that concentrates particulates toward the center of a central channel through the particulate separator. Because nozzles 14 aerodynamically focus and accelerate particulates in a fluid stream, virtual impactors 16 placed downstream of nozzles 14 are able to separate particulates very efficiently. By improving the particulate separation efficiency of each of virtual impactors 16, the present invention enables only one layer or row of virtual impactors 16 to carryout the particulate separation, which eliminates the chances of particulates being lost due to impact on surfaces of additional layers or rows of virtual impactors. The present invention further reduces particulate loss on inner surfaces of minor flow passages, by enabling minor flows to advance straight through the minor flow passages upon virtual impaction, without having to change their flow direction.

A separation plate 10 configured in accordance with the dimensions (all in inches) shown in FIGS. 1B and 1C is designed to have a cut size of about 1.0 microns at a flow rate of 35 liters per minute (1 pm). It should be understood that those of ordinary skill in the art may readily optimize separation plate 10 of the present invention to meet a specific cut size requirement at a predefined flow rate. For example, the cut size of a separation plate may be modified by scaling up or down the various structures provided on the separation plate; larger nozzles with proportionally larger virtual impactors are useful in separating larger particulates, while conversely, smaller nozzles with proportionally smaller virtual impactors are useful in separating smaller particulates. The cut size of a separation plate may also be modified by adjusting a flow rate through the separation plate.

With reference to FIG. 1D, for particulates having 1 to 3 micron diameters, it has been found that making the dimension "a" greater than the dimension "b" generally reduces recirculation of a minor flow upon entering minor flow passage 30, which is preferable for efficiently separating a minor flow from a major flow. For larger particulates, it may be preferable to make "b" larger than "a" to reduce pressure drop.

FIG. 1E illustrates modified configurations of a nozzle 14 and a virtual impactor 16, wherein inner walls 26 of fin-shaped projections 24 include a generally concave surface. Accordingly, the width of upstream minor flow passage 30*a* expands from inlet end 32 toward downstream minor flow passage 30*b*, which is defined between the external walls of adjacent virtual impactor bodies 33. This configuration is advantageous in reducing particulate loss onto inner walls 26.

A separation plate of the present invention may be easily modified to process virtually any volume of fluid stream at any flow rate, by varying the number of nozzles 14 and virtual impactors 16 provided on the separation plate. Furthermore, the throughput of separation plate 10 may be almost indefinitely modifiable by increasing or decreasing height "H" of nozzles 14, virtual impactors 16, and virtual impactor bodies 33. It should be noted that height "H" of a separation plate of the invention can be freely increased without a significant increase in particulate loss. This capability is made possible by the design of this virtual impactor that allows minor flows to advance straight through without experiencing any deflected path.

Separation plate 10 of the present invention may be readily incorporated into various particulate separation/concentration apparatus. Referring to FIG. 2A, for example, a virtual impact collector may be formed by placing a cover plate 42 over projections 18, fin-shaped projections 24, and virtual impactor bodies 33 provided on first surface 10*a*. Cover plate 42 and first surface 10*a* cooperatively define a chamber. Inlet ends 14*a* of nozzles 14 provide an inlet through which a particulate-laden fluid stream may enter the chamber. Minor flow passages 30 provide an outlet through which a minor flow may exit the chamber; however, an outlet through which a major flow may exit the chamber may be provided in various other ways. For example, as in FIGS. 1B and 1C, the plurality of orifices 34 defining terminal ends of passageways 36 may be provided through virtual impactor bodies 33. Alternatively, as in FIG. 2A, cover plate 42 may include a plurality of orifices 44 that extend therethrough. Orifices 44 are configured and arranged so that when cover plate 42 is mated with separation plate 10, orifices 44 are disposed between virtual impactors 16 and adjacent to the upstream end of virtual impactor bodies 33, to exhaust major flows flowing around virtual impactors 16 that are blocked by bodies 33, as indicated by the arrow. It should be understood that, in operating the virtual impact collector as described above, those of ordinary skill in the art can provide a suitable flow subsystem for causing a fluid stream to flow through the chamber.

A further example of a virtual impact collector formed in accordance with the present invention is schematically illustrated in FIG. 2B. In this embodiment, separation plate 10 of FIG. 1B is joined at its opposing edges 45 to form a cylinder. The second surface of separation plate 10 forms the inner surface of the cylinder. The cylindrical separation plate 10 is coaxially slid into a tube 46 having two open ends 46*a* and 46*b* to form an annular chamber 47 therebetween. As before, a suitable major flow outlet (not shown) is provided. In operation, particulate-laden fluid streams enter chamber 47 through the inlet ends of the nozzles defined between nozzle projections 18, adjacent to open end 46*a*. Minor flow passages 30 provide an outlet through which a minor flow exits chamber 47. A suitably provided major flow outlet deflects a major flow to either or both of the inner surfaces of the cylindrical separation plate 10 and/or the outer surface of tube 46.

Figure 3A:
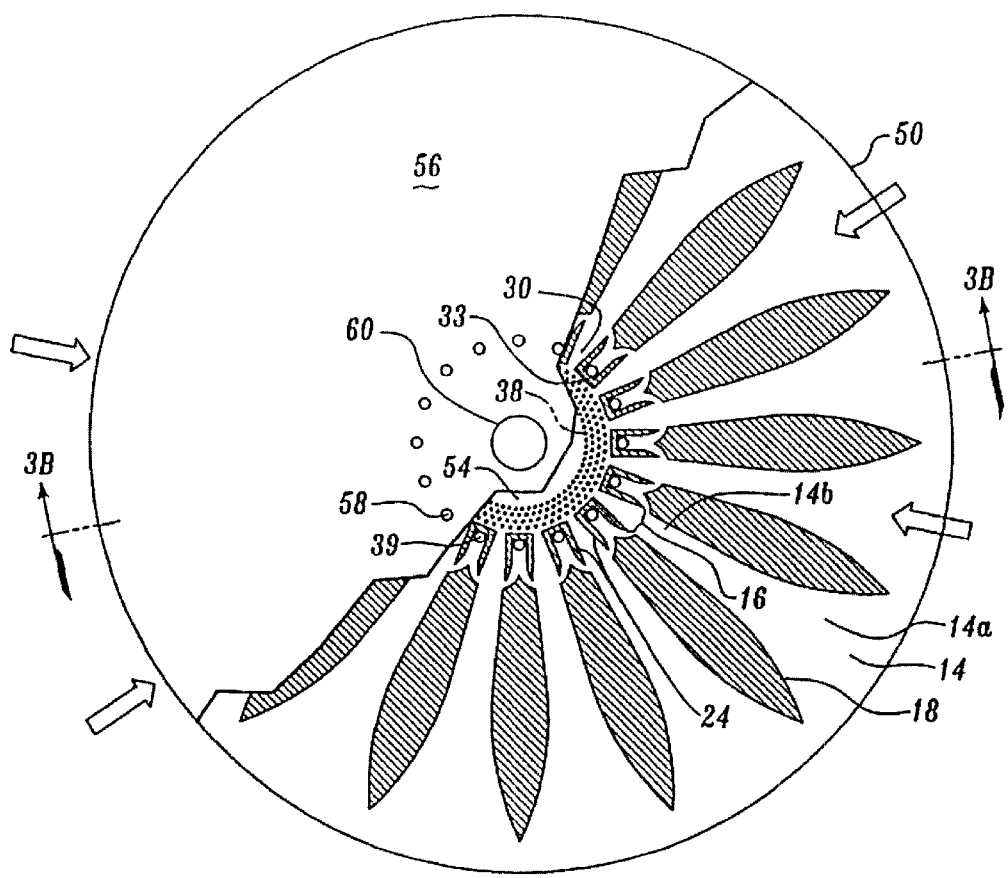
FIG. 3A is a plan view of a virtual impact collector incorporating plural pairs of a nozzle and a virtual impactor arranged radially.
Figure 3B:
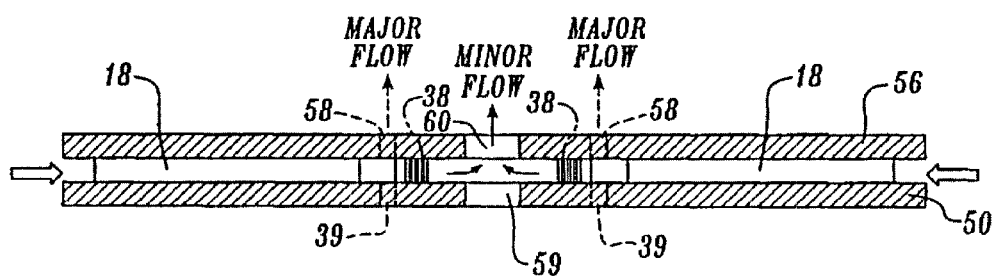
FIG. 3B is a cross-sectional view of the virtual impact collector taken along line 3B—3B of FIG. 3A.

FIGS. 3A and 3B schematically illustrate a radial virtual impact collector including a separation plate 50 and a cover plate 56, in accord with the present invention. Separation plate 50 includes plural pairs of nozzles 14 and virtual impactors 16; the virtual impactors are disposed radially inward of nozzles 14. As before, nozzle 14, which has an inlet end 14a and an outlet end 14b, is defined between adjacent nozzle projections 18. Virtual impactor 16 comprises a pair of fin-shaped projections 24 disposed downstream and radially inward of outlet end 14b of each nozzle 14. As before, fin-shaped projections 24 in each pair are spaced apart and define minor flow passage 30 therebetween. Also as before, a plurality of virtual impactor bodies 33 in the form of a wall extend between the downstream ends of fin-shaped projections 24 of adjacent virtual impactors 16. A plurality of orifices 39 are provided through separation plate 50 radially outward of virtual impactor bodies 33 and between fin-shaped projections 24 of adjacent virtual impactors 16. Virtual impactors 16 and bodies 33 together define a central minor flow collection portion 54. A plurality of impactor pillars 38 are disposed radially inward and downstream of minor flow passages 30, within central minor flow collection portion 54. Impactor pillars 38 are employed to receive a minor flow and to collect particulates thereon, as more fully described below. A minor flow outlet 59 is provided through separation plate 50 near the center of central minor flow collection portion 54. Separation plate 50, which is described above, may be combined with cover plate 56 to form the virtual impact collector. Cover plate 56 is configured to mate with separation plate 50 to define a chamber therebetween. Cover plate 56 optionally include holes 58 that are configured and arranged so that when separation plate 50 and cover plate 56 are combined, holes 58 are aligned to coincide with holes 39 defined through separation plate 50. Optionally, cover plate 56 may include a minor flow outlet 60 defined therethrough. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particulate-laden fluid streams enter nozzles 14 through inlet ends 14a and advance radially inward. When aerodynamically focused fluid streams advance toward virtual impactors 16, they are separated into a minor flow and a major flow, as described above. The major flow flows around virtual impactors 16, is redirected by bodies 33, and is exhausted through either or both of holes 39 in separation plate 50 and/or holes 58 in cover plate 56. The minor flow advances through minor flow passages 30 into central minor flow collection portion 54. When impactor pillars 38 are provided, some of the particulates entrained in the minor flow may impact and become deposited on impactors 38. The particulates collected on impactor pillars 38 may be subsequently collected, for example, by washing impactor pillars 38 with a small amount of liquid to capture the particulates therein. An example of impactors suitable for use in conjunction with the present invention can be found in copending U.S. patent application Ser. No. 09/191, 979, filed Nov. 13, 1998, concurrently with the parent case hereof, and assigned to the same assignee, which is herein expressly incorporated by reference. The minor flow may be exhausted from central minor flow collection portion 54 through either or both of minor flow outlets 59 and 60.

When both minor flow outlets 59 and 60, and both holes 39 and 58 are provided, as illustrated in FIG. 3B, a plurality of the virtual impact collectors described above may be stacked together to process large amounts of fluid streams. The stacked virtual impact collectors include a common minor flow exhaust conduit comprising minor flow outlets 59 and 60, and a common major flow exhaust conduit comprising holes 39 and 58.

Figure 4A:
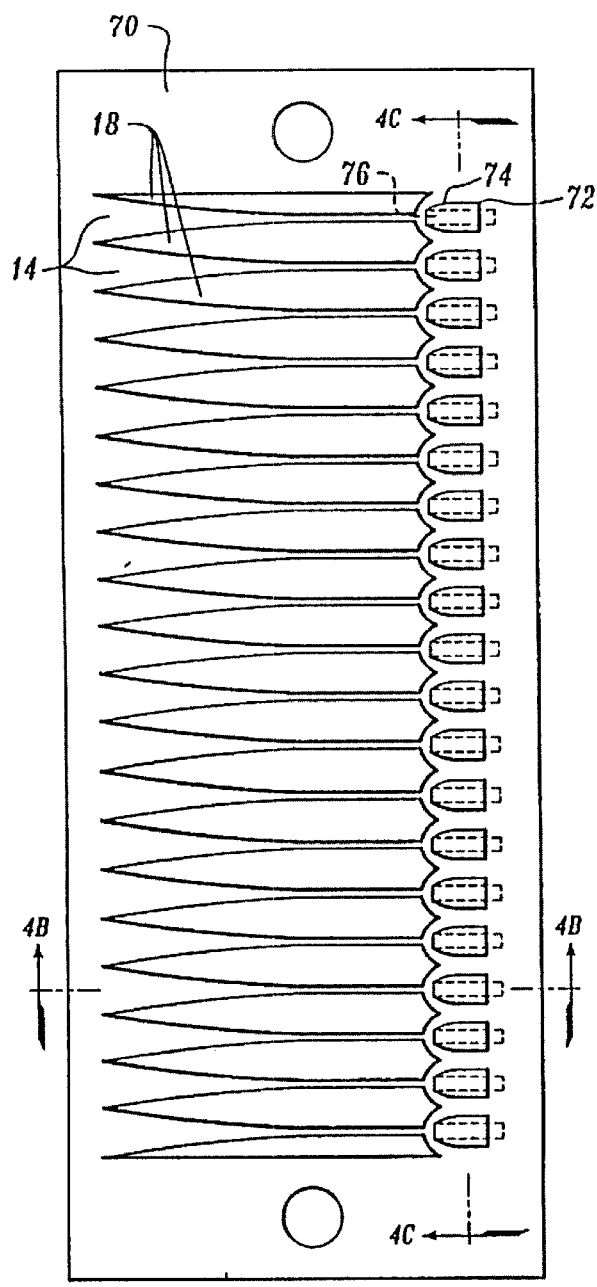
FIG. 4A is a plan view of another configuration of a separation plate in accordance with the present invention.
Figure 4C:
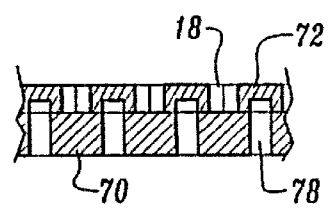
FIG. 4C is a cross-sectional view of the separation plate taken along line 4C—4C of FIG. 4A.
Figure 4B:
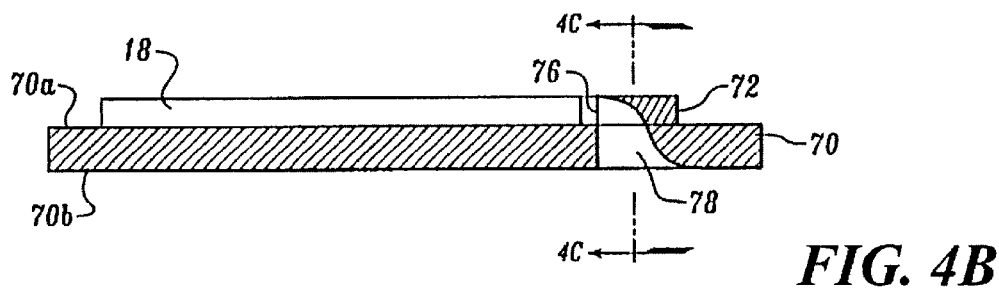
FIG. 4B is a cross-sectional view of the separation plate taken along line 4B—4B of FIG. 4A.

FIGS. 4A, 4B, and 4C illustrate another embodiment of a separation plate 70 in accordance with the present invention. As in the first embodiment, separation plate 70 includes a first surface 70a and an opposing second surface 70b. First surface 70a is provided with a plurality of nozzle projections 18 that define nozzles 14 therebetween. As before, nozzle 14 tapers from an inlet end 14a to an outlet end 14b. Downstream of each outlet end 14b, a generally haystack-shaped virtual impactor projection 72 is provided. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70b of separation plate 70. Alternatively, minor flow passage 78 and virtual impact void 76 may be formed by drilling a hole through separation plate 70. When drilling a hole, minor flow passage 78 preferably passes through separation plate 70 at an acute angle so that a minor flow containing a major portion of particulates will avoid sharp changes in direction upon entering virtual impact void 76. It should be noted that the longer minor flow passage 78, the more particulates may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 is to be determined based partly on the limitations imposed by the available micro-machining methods. An angle of between approximately 15° and 45°, which is possible with currently available micro-machining methods, should provide satisfactory results.

In operation, particulate-laden fluid streams flow along first surface 10a through nozzles 14 and advance toward convex surfaces 74 of virtual impactor projections 72. Major flows continue around projections 72 to avoid obstruction presented by convex surfaces 74, and flow along first surface 10a. Minor flows are collected in a zone of stagnant fluid created near convex surfaces 74, and enter virtual impact voids 76 defined through convex surfaces 74. The minor flows travel through minor flow passages 78 to second surface 70b, where they can be collected, and analyzed or processed after being archived, as discussed below. Thus, unlike separation plates 10 and 50 of the previous embodiments, separation plate 70 of the present embodiment separates a particulate-laden fluid stream into a minor flow on the second surface, and a major flow on the first surface.

Another embodiment of a separation plate 100 is illustrated in FIGS. 5A and 5B. A separation plate 100 includes a central passage 102 that extends laterally across the length of the separation plate and through its width. The passage is defined between plates 104a and 104b and is machined within the facing surfaces of these two plates, which preferably comprise a metal such as steel, aluminum, or titanium, or a another suitable material such as plastic. Alternatively, the passage can be formed by molding or casting the plates from metal, or another suitable material, such as plastic. Passage 102 is readily formed in the surfaces of each of plates 104a and 104b by conventional machining techniques. Since the surfaces are fully exposed, the desired telescoping or converging configuration of the passage is readily formed. The passage extends from an inlet 108, which is substantially greater in cross-sectional area due to its greater height compared to that of an outlet 106. The outlet is disposed on the opposite side of the separation plate from the inlet. Inlet 108 tapers to a convergent nozzle 110, which further tapers to the opening into a minor flow portion 112 of passage 102.

In this preferred embodiment of separation plate 100, one-half of the thickness of passage 102 is formed in plate 104a, and the other half of the thickness of the passage is formed in plate 104b. However, it is also contemplated that the portions of the passage defined in each of plates 104a and 104b need not be symmetrical or identical, since a desired configuration for passage 102 can be asymmetric relative to the facing opposed surfaces of the two plates.

Immediately distal of the point where minor flow portion 112 of passage 102 begins, slots 115a and 115b are defined and extend transversely into the plates relative to the direction between the inlet and the outlet of passage 102 and extend laterally across separation plate 100 between the sides of the passage. Slots 115a and 115b respectively open into major flow outlet ports 114a and 114b in the ends of plates 104a and 104b, as shown in FIG. 5A. Threaded fastener holes 116 are disposed on opposite sides of each of major flow outlet ports 114a and 114b and are used for connecting a major flow manifold (not shown) that receives the major flow of fluid in which the minor portion of the particulates greater than the cut size is entrained.

Fastener holes 118a are formed through plate 104b adjacent to its four corners and do not include threads. Threaded fasteners (not shown) are intended to be inserted through holes 118a and threaded into holes 118b, which are formed at corresponding corner positions on plate 104a. The threaded fasteners thus couple edge seals 120 on the two plates together, sealing the edges of passage 102 and connecting plates 104a and 104b to form separation plate 100. Although not shown, a manifold may also be connected to the back surface of separation plate 100 overlying outlet 106 to collect the minor flow of fluid in which the major portion of particulates exceeding the cut size is entrained. In FIG. 5A, the flow of fluid entering inlet 108 of passage 102 is indicated by the large arrow, the major flow exiting major flow ports 114a and 114b is indicated by the solid line arrows, and the minor flow exiting outlet 106 of passage 102 is indicated by the dash line arrow. The cross-sectional profile of passage 102 as shown in FIG. 5B focuses the particulate-laden fluid flow entering inlet 106 for delivery to the receiving nozzle and thus performs in much the same way as the profile used in the previous embodiments of virtual impactors.

The desired flow through the separation plate will determine the width of passage 102, as measured along the longitudinal axis of the separation plate, between sealed edges 120. Additional fluid flow can also be accommodated by providing a plurality of the separation plates in an array, which will also avoid using extremely long and thin structures that may not fit within an available space. FIG. 5B illustrates two such additional separation plates 100' and 100", stacked on each side of separation plate 100, so that the fluid enters the inlets of the stacked separation plates and is separated in the major flow and the minor flow exiting the separation plates, as described above.

FIGS. 6A and 6B illustrate still another embodiment of a separation plate 200 that is similar to separation plate 100, which was discussed above in regard to FIGS. 5A and 5B. Separation plate 200 differs from separation plate 100 in at least two significant ways, as will be apparent from the following discussion. To simplify the following explanation of separation plate 200, the reference numbers applied to its elements that are similar in function to those of separation plate 100 are greater by 100. Thus, like central passage 102 in separation plate 100, separation plate 200 includes a central passage 202 that extends laterally across the length of the separation plate and through its width. The passage is defined between plates 204a and 204b and is machined within the facing surfaces of these two plates, which also preferably comprise a metal such as steel, aluminum, or titanium formed by machining or by molding the plates from metal, or another suitable material, such as a plastic. The passage extends from an inlet 208, which is substantially greater in cross-sectional area due to its greater height, to an outlet 206 disposed on the opposite side of the separation plate from the inlet. Unlike inlet 108 of the previous embodiment, which tapers to a convergent nozzle 110 and then to a minor flow portion 112 of passage 102, the central passage in separation plate 200 does not taper to smaller cross-sectional sizes. Instead, the central passage in separation plate 200 changes abruptly to a smaller cross-sectional size at a step 222, continuing through a section 210, and then again decrease abruptly to a smaller minor flow outlet 212, at a step 224. At each of steps 222 and 224, a swirling flow or vortex 226 of the fluid is produced. It has been empirically determined that these vortexes tend to focus the particulates toward the center of the passage, thereby providing a substantial improvement in the efficiency with which the particulates smaller than the cut size are separated from the particulates larger than the cut size.

In this preferred embodiment of separation plate 200, one-half the thickness of passage 202 is formed in plate 204a, and the other half of the thickness of the passage is formed in plate 204b, just as in the previous embodiment. And again, it is contemplated that the portions of the passage defined in each of plates 204a and 204b need not be symmetrical or identical, since a desired configuration for passage 202 can be asymmetric relative to the facing opposed surfaces of the two plates.

Immediately distal of the point where minor flow portion 212 of passage 202 begins, slots 215a and 215b are defined and extend transversely into the plates relative to the direction between the inlet and the outlet of passage 202 and extend laterally across separation plate 200 between the sides of the passage, just as in separation plate 100. Slots 215a and 215b respectively open into major flow outlet ports 217a and 217b, which are open to the ends and outer surfaces of plates 204a and 204b, as shown in FIG. 6A. In this embodiment, separation plate 200 is designed to be stacked with other similar separation plates 200' and 200", as shown in FIG. 6B, so that adjacent separation plates cooperate in forming the passage for conveying the major flow into an overlying major flow manifold (not shown). It is also contemplated that separation plate 100 can be configured to include major flow outlet ports similar to those in separation plate 200. The last plate disposed at the top and bottom of a stack of separation plates configured like those in FIG. 6B would include major flow outlet ports 114a and 114b, respectively. Threaded fastener holes 216 are disposed on opposite sides of each of major flow outlet ports 217a and 217b and are used for connecting a major flow manifold (not shown) that receives the major flow of fluid in which the minor portion of the particulates greater than the cut size is entrained.

Fastener holes 218a are formed through plate 204b adjacent to its four corners and do not include threads. Threaded fasteners (not shown) are intended to be inserted through holes 218a and threaded into holes 218b, which are formed at corresponding corner positions on plate 204a. The threaded fasteners thus couple edge seals 220 on the two plates together, sealing the edges of passage 202 and connecting plates 204a and 204b to form separation plate 200. Although not shown, a manifold may also be connected to the back surface of separation plate 200 overlying outlet 206 to collect the minor flow of fluid in which the major portion of particulates exceeding the cut size is entrained, for use in creating an archive of the samples thus collected as explained below. In FIG. 6A, the flow of fluid entering inlet 208 of passage 202 is indicated by the large arrow, the major flow exiting major flow outlet ports 217a and 217b is indicated by the solid line arrows, and the minor flow exiting outlet 206 of passage 202 is indicated by the dash line arrow.

Separation plates 100 and 200 costs less to manufacture than the other embodiments discussed above. As was the case with separation plate 100, the desired flow through the separation plate will determine the width of passage 202 along the longitudinal axis of the separation plate, between sealed edges 220, and additional fluid flow can also be accommodated by providing a plurality of the separation plates in an array configured to fit within an available space. FIG. 6B illustrates two additional separation plates 200' and 200", stacked on opposite sides of separation plate 200, so that the fluid enters the inlets of the stacked separation plates and is separated in the major flow and the minor flow exiting the separations plates, as described above.

Figure 7:
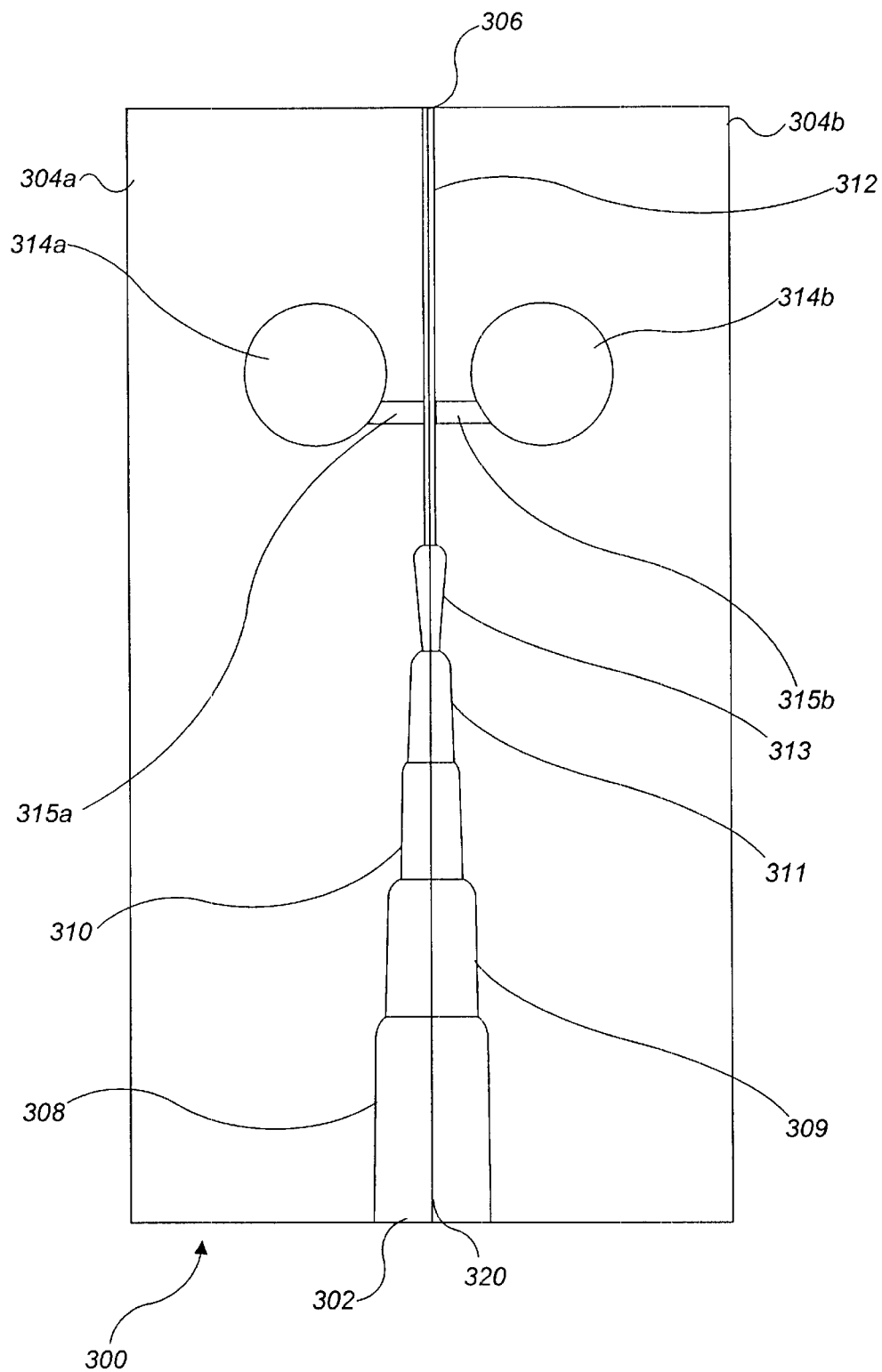
FIG. 7 is a cross-sectional view of a separation plate like that shown in FIGS. 5A and 5B, but having a slightly modified passage through which the fluid flows to optimize the efficiency of separation over a broader range of particulate sizes.

Finally, yet another embodiment of the present invention, a separation plate 300 is illustrated in FIG. 7. Separation plate 300 is also similar to separation plate 100, which is shown in FIGS. 5A and 5B, but includes a central passage 302 that differs from central passage 102 in separation plate 100. Again, to simplify the following explanation, reference numbers applied to the elements of separation plate 300 that are similar in function to those of separation plate 100 are greater by 200. It will thus be apparent that central passage 102 in separation plate 100 corresponds to central passage 302 in separation plate 300 and that central passage 302 extends laterally across the length of separation plate 300 and through its width. The passage is defined between plates 304a and 304b and is machined within the facing surfaces of these two plates, preferably from a metal such as steel, aluminum, or titanium formed by machining, or by molding the plates from metal, or another suitable material, such as a plastic. The passage extends from an inlet 308, which is substantially greater in cross-sectional area due to its greater height, to an outlet 306 disposed on the opposite side of the separation plate from the inlet. Central passage 302 comprises a telescoping section that performs aerodynamic focusing of the particulates so as to achieve a further optimization in maximizing the efficiency of the separation plate over a wider range of particulates sizes, compared to the other embodiments. The focusing is accomplished in this embodiment by using a combination of contracting and diverging sections. Specifically, an inlet 308 tapers slightly at its distal end to a more convergent section 309, which again tapers to a convergent nozzle 310, which further tapers at its distal end to another convergent section 311. The distal end of convergent section 311 tapers into the proximal end of a divergent section 313, and its distal end then tapers into a minor flow portion 312 of central passage 302. Distal of the point where minor flow portion 312 of central passage 302 begins, slots 315*a* and 315*b* are defined and extend transversely into the plates relative to the direction between the inlet and the outlet of central passage 302 and extend laterally across separation plate 300 between the sides of the passage. Major flow outlet ports 314*a* and 314*b* can be used for connecting to a major flow manifold (not shown) that receives the major flow of fluid in which the minor portion of the particulates greater than the cut size is entrained.

As will be apparent from the preceding description, a number of gentler steps are used in the central passage of separation plate 300 than in the preceding embodiments of FIGS. 5A and 5B, and 6A and 6B, to improve the efficiency of separating larger particulates (i.e., approximately 5$\mu$ to 10$\mu$ in size); larger particulates tend to have greater wall losses due to impaction on the "steps" of the telescoping profile. The gentler steps will not focus the small particulates as well as in the other embodiments, however, so the outward expansion provided by diverging section 313, followed by a final steep step into minor flow passage 312 to focus the small particulates seems to improve the efficiency of the separation (at least in simulations). The flow of larger particulates does not expand out much in diverging section 313, and is thus less likely to impact on the final step into minor flow passage 312.

In all other respects, separation plate 300 operates like separation plate 100, and can be modified to collect the major flow like separation plate 200. It will also be apparent that a plurality of separation plates 300 can be stacked, just as in the previous embodiments, to increase the volume of fluid processed.

Particulate Collection

Once the particulate concentration of the fluid stream has been enhanced by the use of a virtual impactor as described above, collection of the concentrated particulates can be effected. It should be noted that impact based collectors (as opposed to the virtual impact collectors described above) can also achieve significant particulate concentrations. However, the impact surface portion of such impact collectors is generally an integral portion of the impact collector, and it is not practical to archive the impact collector itself. The collection surface of impact collectors is generally rinsed with a fluid to obtain the collected particulates for analysis. While such particulates collected in that fashion could also be archived, the volume of fluid required to rinse the collected particulates from the impact collector significantly increases the volume of material that must be archived. Furthermore, the steps of rinsing, collecting, and storing the rinsate add significant time and effort (and thus cost) to archiving particulates. The use of a virtual impactor enables an archival surface to be employed that is a separate component. Such a separate component can be readily removed from the virtual impactor and replaced with a fresh surface for collecting particulate samples. The archival surface on which the sample have been collected can then be stored without significant additional processing until needed.

Any surface material amenable to spot deposition can be used. The present invention contemplates several different deposition methods. A first method involves directing the minor flow described above toward a filter through which the fluid in the minor flow can pass and upon which the particulates are deposited. In a different embodiment, the particulates are directed toward an impaction surface that is enveloped in a vacuum system. The archival (impaction) surface can also be coated with a material that aids in the deposition and retention of particulates that have impacted on the surface.

Figure 8:
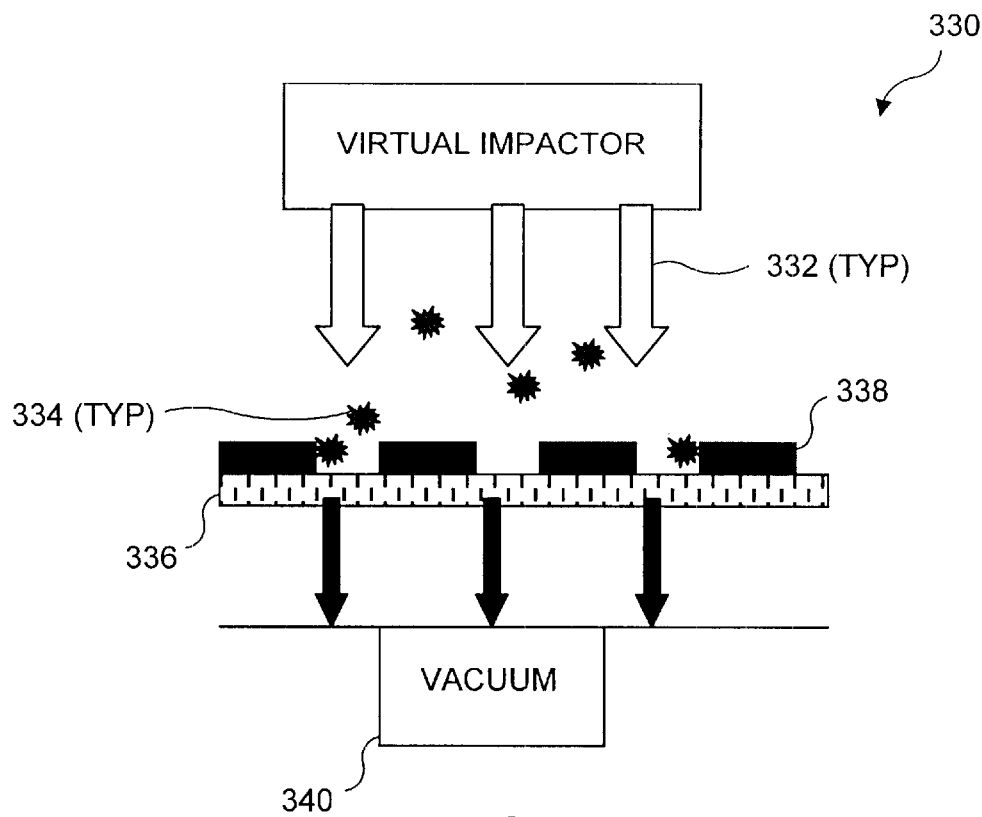
FIG. 8 is a schematic view of a porous archival impaction surface in accord with one embodiment of the present invention.

FIG. 8 schematically illustrates an archival collection system 330 that uses a porous hydrophilic filter medium 336 as the deposition surface. Preferably a hydrophobic material 338 would be deposited on top of porous hydrophilic filter medium 336. Openings 342 in hydrophobic material 338 direct particulates 334 entrained in a minor flow 332 toward locations on porous hydrophilic filter medium 336 that particulates will be collected upon. The fluid in which the particulates are entrained passes through the porous hydrophilic filter medium 336, leaving the particulates deposited on the surface. A vacuum source 340 can be beneficially employed to ensure that the minor flow fluid passes through the porous filter, rather than being diverted around sides of the porous filter.

Preferably the area between the introduction of the minor flow and the filter is sealed, so the particulates will not be lost prior to impact. The sealing preferably extends between the bottom of the porous filter and vacuum source 340. While not readily apparent from FIG. 8, it should be understood that porous hydrophilic filter medium 336 moves relative to the position of the minor flow, so that particulates collected from the minor flow at different times are associated with different (and known) locations on the porous filter. In general, it is anticipated that it will be simpler to move the archival surface than the virtual impactor, although movement of either the virtual impactor or the archival surface will enable particulates to be deposited on specific spaced-apart portions of the archival surface as a function of time. Regardless of which component is moved, preferably any sealing system employed should be capable of accommodating the required movement.

Figure 9:
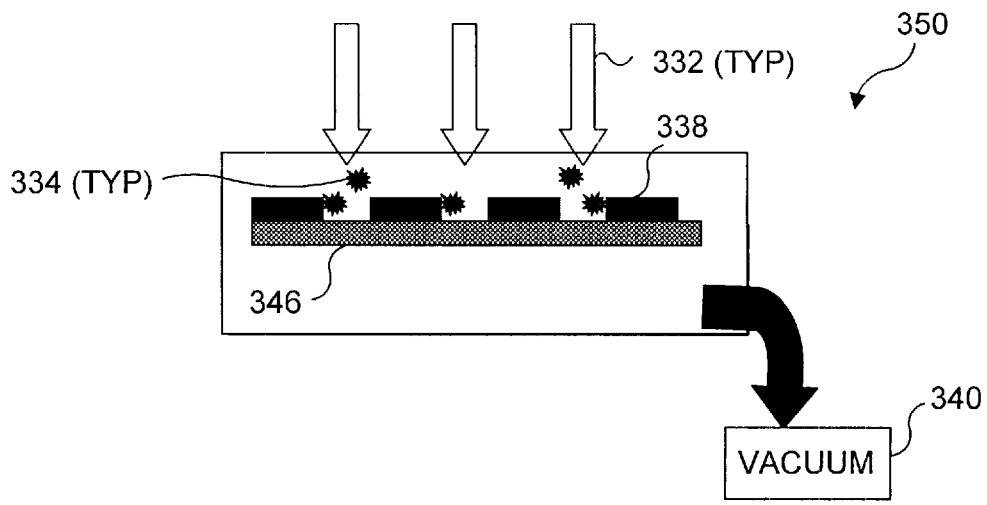
FIG. 9 is a schematic view of a non-porous archival impaction surface in accord with another embodiment of the present invention.

As shown in FIGS. 8 and 9, the minor flow is directed towards the archival surface as three separate streams. It should be understood that either few or more than three minor flow streams could alternatively be employed as well. The benefit of employing multiple minor flows is that, as described above, individual virtual impactors can be fabricated to selectively direct particulates of a desired size into the minor flow. Thus, by employing a plurality of virtual impactors, each concentrating a different particulate size into their respective minor flows, particulates of different sizes can be directed onto different locations of an archival surface. Alternately, particulates of the same size can be deposited in different locations, permitting duplication of sampling to occur, to facilitate multiple testing, perhaps at different times.

FIG. 9 schematically illustrates an archival collection system 350 that uses a non-porous archival surface 346 as the deposition surface. In archival collection system 350, the particulate-laden fluid is accelerated through a minor flow outlet nozzle of a virtual impactor to impact the surface. Preventing particulates from bouncing off of non-porous archival surface 346 is a key aspect of this approach.

Note that in both FIGS. 8 and 9, a surface coating or layer has been applied on top of the archival surface to define receptacles for spots. Such a coating (hydrophobic material 338) is not required, but is a useful addition. Regardless of whether a porous or non-porous archival surface is employed, several different surface treatments may be useful in increasing the efficiency of spot formation. For example, a common problem with surface impaction is that particles bounce off the surface, return to the fluid stream, and are swept away. It is preferable to coat the surface to promote particle adhesion. Such surface coatings include, but are not limited to, charged chemical species, proteins, and viscous substances that increase the impact force required to enable the particulates to bounce away from the archival surface. Details of exemplary coatings that can be beneficially employed in the present invention are described below. It should be noted that a person skilled in the art will recognize that many other coatings, having other physical and chemical properties, can be beneficially employed to aid in the collection of specific types of particulates. In at least one embodiment, the coating is on the order of 100 microns thick, while the archival surface itself is in the order of 100 mm thick.

It should be noted that the archival surface, with or without a coating, need not be flat. Preferentially, a surface with portions raised significantly above the bulk of the surface can also be used collect spots of particulates. For example, a textured surface with portions raised substantially above a background portion of the surface can be used to collect spots of particulates. Such textured surfaces are disclosed in commonly assigned U.S. Pat. No. 6,110,247, the disclosure and drawings of which are hereby specifically incorporated herein by reference. Such surfaces reduce the tendency of particles to bounce and therefore increase spot formation efficiency.

Archival Surface Coatings

Figure 10:
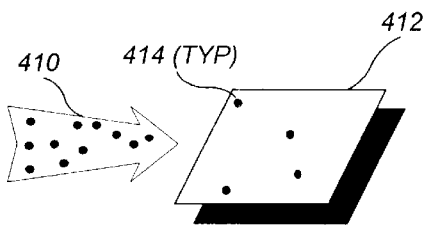
FIG. 10 (prior art) is a schematic view of a fluid in which particulates are entrained, showing the particulates impacting an uncoated impact collection surface.
Figure 11:
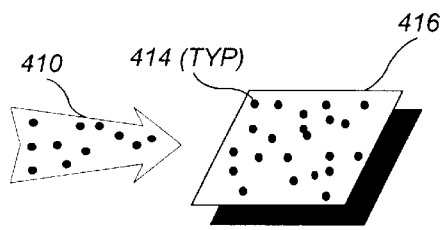
FIG. 11 is a schematic view of a fluid in which particulates are entrained, showing the particulates impacting a coated impact collection surface in accord with the present invention.

FIGS. 10 and 11 schematically illustrate how coating an impact collection surface, such as an archival surface, with a material can substantially enhance the efficiency of that surface. FIG. 10 shows a fluid 410 in which particulates 414 are entrained, moving relative to a (prior art) impact collection surface 412 that is not coated. Particulates 414 are separated from the fluid by striking against impact collection surface 412. FIG. 11 shows fluid 410 moving toward a coated impact collection surface 416, which has been coated with a material that retains substantially more of the particulates entrained in fluid 410 than would an uncoated surface. By comparison of these FIGS. 10 and 11 it will be apparent that substantially more particulates 414 are collected on coated impact collection surface 416 than on impact collection surface 412.

The relatively greater density of particulates 414 evident on coated impact collection surface 416 compared to impact collection surface 412 is due to a characteristic of the coating that causes it to better retain particulates and thus more efficiently separate the particulates from the fluid in which they are entrained, compared to the prior art impact collection surface that is not coated. In the embodiment of the present invention shown in FIG. 11, the geometry of impact collection surface 416 is generally irrelevant. The coating of the present invention can be applied to the impact collection surfaces in almost any impact collector or virtual impact collector. Simply by coating surfaces on which a stream of particles impacts with one of the materials described below, a substantial increase in the efficiency with which the particulates are separated from a fluid and collected is achieved.

Figure 12:
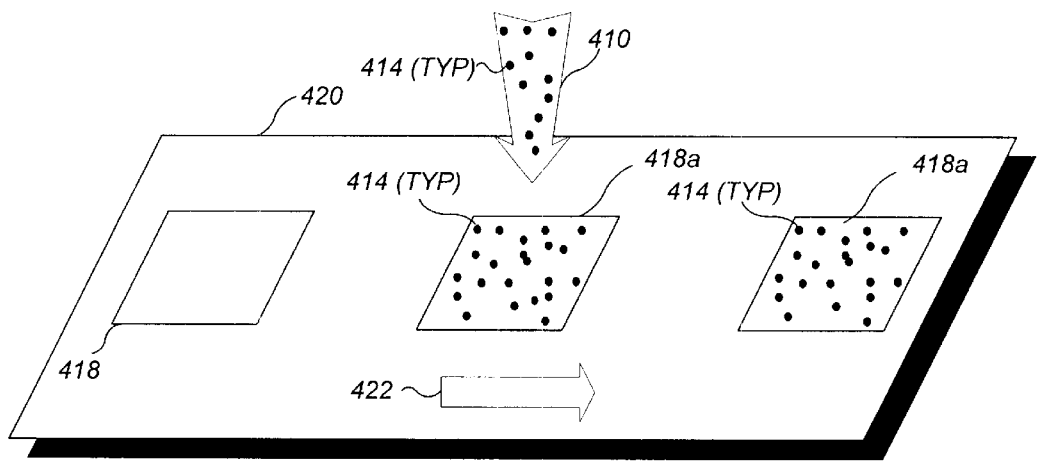
FIG. 12 is a schematic view of a flexible tape having a partially coated impact collection surface.

FIG. 12 schematically illustrates an embodiment of the present invention in which a plurality of coated areas 418 are applied to an upper exposed surface of an elongate tape 420. As illustrated in this Figure, tape 420 is advanced from left to right, i.e., in the direction indicated by an arrow 422. Tape 420 thus moves past a stream 421 of fluid 410 in which particulates 414 are entrained. Stream 421 is directed toward the upper surface of the tape. As the tape advances, fresh coated areas 418 are exposed to impact by particulates 414.

The particulates that impact on these coated areas are at least initially retained thereon, as shown in coated areas 18a. In the embodiment illustrated in FIG. 12, coated areas 418 and 418a are not contiguous, but instead are discrete patches disposed in spaced-apart array along the longitudinal axis of tape 420. Various types of material described below can be used to produced coated areas 418.

Figure 13:
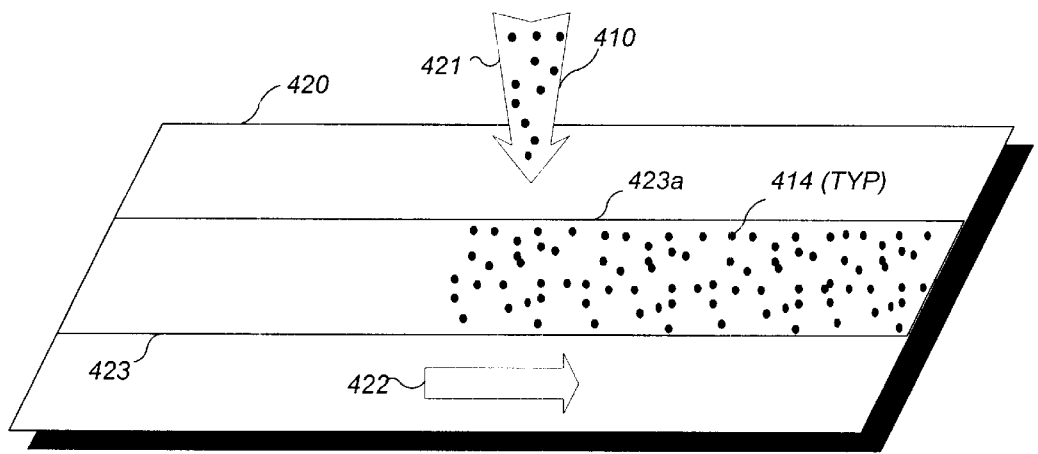
FIG. 13 are schematic views of a flexible tape having a continuously coated impact collection surface.

In an alternative embodiment shown in FIG. 13, a continuous coated impact collection surface 423 extends longitudinally along the center of a tape 420'. As tape 420' advances in the direction indicated by arrow 422, stream 421 of fluid 410 with entrained particulates 414 is directed toward the upper surface of the tape. Particulates 14 are retained by the coating, as shown in a coated impact collection surface 423a. As tape 420' advances in direction 422, coated impact collection surface 423 is exposed to impact by particulates 414 carried in stream 421. In the embodiment that is illustrated, the coating does not cover the entire upper surface of tape 420'. However, it should be understood that any portion or the entire upper surface of tape 420' can be covered with the coating.

The material used for producing coated impact collection surface 423 and other coated areas or surfaces employed in this description for collecting particulates in accord with the present invention is selected because of certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in collecting particulates in a dry air or other dry fluid, a material called TETRAGLYME can be used to for the coating. This material is hydrophilic until it is exposed to water and when dry, is relatively very sticky, tending to readily retain particulates that impact it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface. TETRAGLYME, which is available from chemical supply houses, is bis(2-methoxyethoxy) ethyl ether (also referred to as tetraethylene glycol dimethyl ether) and has the formula: $CH_3(OCH_2CH_2)_4OCH_3$. Tests have shown that TETRAGLYME coating can collect more than three times as many particulates as an uncoated surface. Water molecules are retained by the molecule by links to the oxygen atoms, as shown below.

$$O:H_2O:O$$

A second type of material usable for a coated particulate collection surface is parylene, which is a tetrafluoromore manufactured and sold by DuPont Chemical Company under the trademark INSUL-COTE™, Type N. The parylene material is characterized by a relatively low coefficient of friction, causing it to be extremely slippery and not sticky. Accordingly, particulates impacting against a coated surface comprising parylene are initially separated from the fluid in which they are carried by the impact with the coated surface and are initially retained by the coated surface. However, these particulates are readily washed away from the parylene coated surface by water or other liquid sprayed onto the coating. The particulates retained by a parylene coated surface on tape 420' are readily washed away from the coating by water or other liquid spray.

The TETRAGLYME material is an example of a class of materials that has two distinct states related to particulate collection. When dry and hydrophilic, the TETRAGLYME material is in a first state, in which it is sticky and is very efficient at separating particulates from the fluid in which they are entrained, compared to an uncoated surface. However, when wetted, the TETRAGLYME material changes to its second state, in which it readily releases the particulates.

Figure 14:
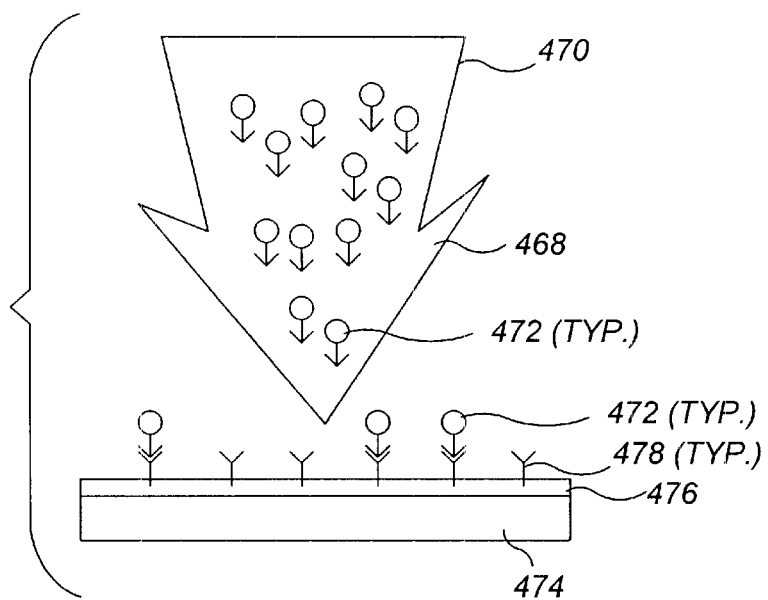
FIG. 14 is a schematic illustration illustrating an impact collection surface coated with a material that includes antibodies selected to link with an antigen on a specific biological particulate.

As shown in FIG. 14, a mono-layer material 476 can be applied to a surface 474 of a particulate collector to separate specific biological particulates 472 from a fluid 468 such as air or a liquid in which they are entrained. It is contemplated that the fluid conveying the biological particulates may also include blood. A stream 470 of the biological particulates is directed at material 476, so that the biological particulates impact thereon. Mono-layer material 476 comprises a plurality of antibodies 478 that are selected to link with the antigens on biological particulates 472. For example, if biological particulates 472 comprise anthrax spores, and antibodies 478 are selected that are specific to anthrax spores, the anthrax spores will be readily separated and retained by linking with the antibodies on the coating. These anthrax spores may then be identified based upon an appropriate analysis. The type of analysis employed is outside the scope of this disclosure. Those of ordinary skill in the art will recognize that based on the nature of the targeted particulates, that a specific analytical procedure may be more or less appropriate.

Figure 15A:
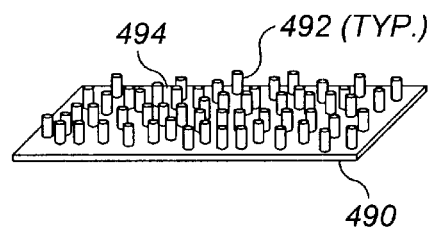
FIGS. 15A and 15B illustrate two embodiments in which outwardly projecting structures are provided on an impact collection surface to enhance particulate collection.
Figure 15B:
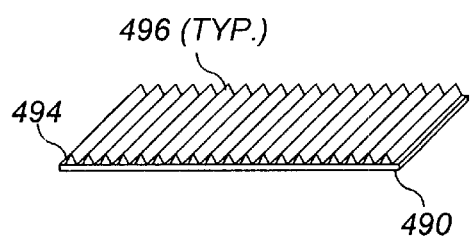
Figure 16:
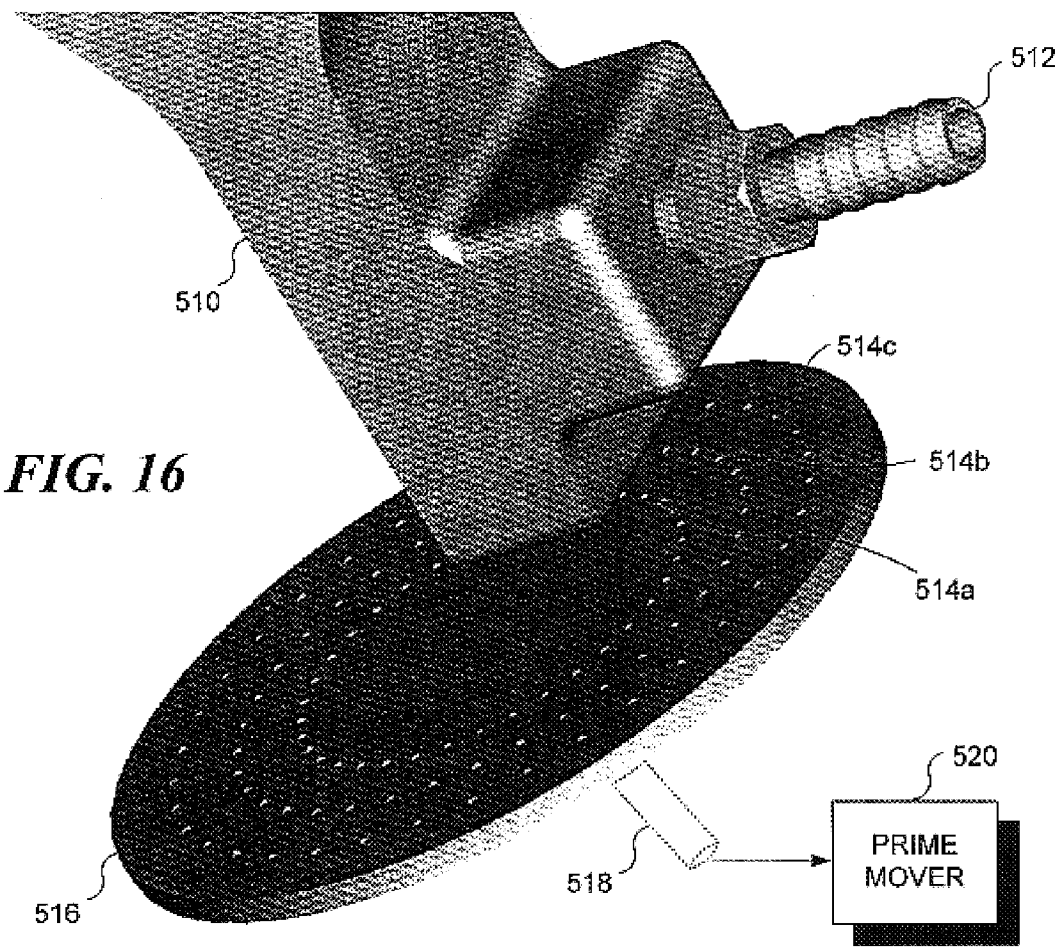
FIG. 16 is an isometric view of a virtual impactor and an archival surface in accord with the present invention.
Figure 17A:
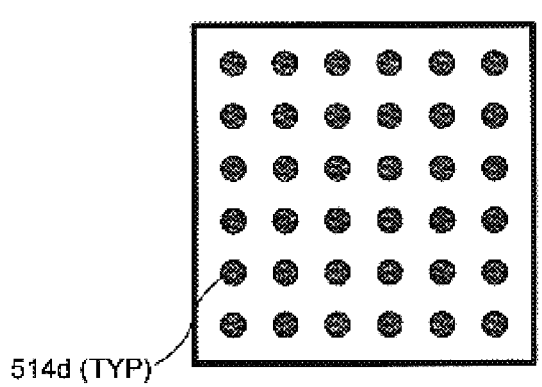
FIGS. 17A and 17B illustrate two embodiments of archival surfaces, each having a different pattern of archival spots.
Figure 17B:
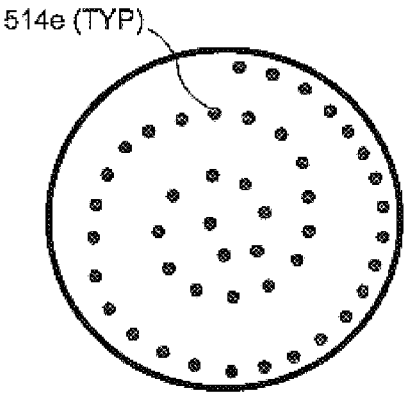

It is also contemplated that the coated impact collection surface need not be planar. Indeed, it is likely that an enhanced particulate collection efficiency can b achieved by using a non-planar coated surface to collect particulates. FIG. 15A illustrates an enlarged view of a portion of one preferred embodiment for a textured particulate collection surface 490 having a plurality of outwardly projecting rods 492 distributed thereon. The outwardly projecting rods increase the surface area of particulate collection surface 490, which is provided with a coating 494 of one of the coating materials discussed above, and also increase the "roughness" of the surface to further enhance the collection efficiency of the coating. Coating 494 may be applied over rods 492 or applied before the rods are attached. Alternative, other projecting structures such as ribs 496 may be employed on textured particulate collection surface 490, as shown in FIG. 15B.

In at least one embodiment, the archival surface incorporates a material that helps maintain the particulates deposited on the archival surface in good condition, without substantial degradation. For some particles, such as living cells, this material may be a liquid that contains nutrients. Applying a hydrogel or equivalent coating on the archival surface would allow localization of water. The water can be used to deliver salts, sugars, proteins, and other nutrients to enable the cells to survive on the archival surface during the time interval between deposition on the archival surface and subsequent analysis of the collected samples of particulates.

For all of the above surfaces, some portion of the analysis/detection scheme could be included as part of the surface. For example, if the analysis employed to detect a specific particulate involves incubating the collected particulates (some of which are likely to be bioparticles) with a reagent, the reagent can be incorporated onto the surface so that the incubation period is initiated upon deposition.

Orientation of Archival Surface Relative to Virtual Impactor

As noted above, because the location of a "spot" of particulates deposited on the archival surface is indicative of a time the particulates were collected, it is preferable to move the archival surface relative to the virtual impactor, at least at spaced-apart times to form spots of particulates (or continually to form streaks of particulates). Moving the archival surface at successive time intervals permits multiple sample spots to be deposited on a single archival surface without commingling the spots. The time at which each spot is deposited is associated with the spot. Alternatively, time can be linear in its association with a position in a streak of particles that are deposited continuously.

One embodiment providing for intermittent relative motion between the archival surface and the adjacent stream of particulates is shown in FIG. 16, in which a virtual impactor 510 is fixedly mounted over a movable archival surface that is formed in the shape of a disk 516. The minor flow of particulates is directed at the disk. A major flow 512 containing particulates of non target size exits virtual impactor 510 orthogonally with respect to the minor flow, to prevent particulates entrained in the major flow from being deposited on disk 516. While not shown, it should be understood that disk 516 could be further separated from major flow 512 by a protective housing.

The nozzles directing the minor flow toward disk 516 cannot be seen in FIG. 16, but virtual impactor 510 includes three minor flow outlets, all of which are oriented to direct particulates towards spot deposition areas 514*a*–514*c*. As disk 516 rotates beneath virtual impactor 510, the minor flow nozzles of virtual impactor 510 direct particulates to a new deposition area. Note that disk 516 shows three concentric rings of spaced-apart spots in three different annular deposition areas, area 514*a* defining the inner ring of spots, area 514*b* defining a middle ring of spots, and areas 514*c* defining an outer ring of spots. Disk 516 is preferably indexed (not shown) so that the spots are defined at discrete predetermined positions around the deposition areas, that enable the position of each spot to be associated with a specific time, and enable the particulates to be accurately directed toward the disposition of each spot on the disk. It should be understood from FIG. 16, and the preceding description, that deposition areas 514*a*–514*c* preferably each include a plurality of depressions formed into disk 516, either as openings in a coating on disk 516, or depressions formed into the surface of disk 516, where each spot of particulates is to be deposited. However, while such openings/depressions are anticipated to increase collection efficiency, they are not required.

Disk 516 can be moved using an appropriate prime mover 520, such as a stepping motor. As shown, one such means includes a shaft 518 detachably coupled to disk 516 and driven by prime mover 520. It is anticipated that disk 516 will remain stationary for a desired time interval, and then will be rotated a sufficient amount to align another set of depressions in the deposition areas with the minor flow nozzles of virtual impactor 510, so that the spots of particulates can be deposited within the depressions, if depressions are indeed provided. The virtual impactor can be cycled on and off during the movement if desired.

As noted above, is also possible to deposit streaks of particulates instead of spots. In a more elaborate embodiment, the archival surface is continually moved at a fixed rate, resulting in annular rings defined by streaks of particles on the archival surface, instead of discrete spots. The use of streaks somewhat simplifies the operation of the collector, in that it can operate continuously, rather than being cycled on and off.

Note that more or fewer minor flow nozzles can be incorporated into a virtual impactor. Preferably, each virtual impactor minor flow nozzle will be directed to a different location on the archival surface. It should also be noted that different configurations of archival surfaces can be employed (i.e., shapes other than disks), and that different configurations of spots can be deposited on archival surfaces (i.e., configurations other than streaks or concentric rings of spots). FIG. 17A shows a quadrilateral shaped archival surface on which deposition areas 514*d* are oriented in an array extending orthogonally in two directions. FIG. 17B shows a second disk-shaped archival surface, on which deposition areas 514*e* are oriented in a spiral array. It should be understood that any of deposition array 514*a*–514*e* illustrated and discussed above can be one or more of: (1) a depression on the archival surface; (2) an opening in a coating on an archival surface; (3) an aggregate of particulates deposited in a spot; and (4) an area in which an aggregate of particulates are to be deposited without regard to the shape of the deposit.

Exemplary Archival Collection System

FIG. 18 illustrates an exemplary archival system 530, for collecting and archiving particulates entrained in a flow of fluid. Such particulates can include chemical and biological compounds. System 530 includes a fluid inlet 531 that diverts a portion of a flow of fluid into system 530. A fan 533, which can be centrifugal fan or an axial fan driven by a motor or other prime mover, forces fluid through system 530. It should be noted that the virtual impactors used in the present invention to separate a flow of fluid into minor and major flows function best when the fluid passes through the virtual impactor at about a predefined velocity. While a source of some fluid streams may have sufficient velocity to pass through a virtual impactor without requiring a fan to drive them through the virtual impactor, it is contemplated that many applications of system 530 (such as collecting particulates from a smokestack) will require fan 533. While as shown, fan 533 forces a fluid into system 530, those of ordinary skill in the art will recognize that the fan could alternatively be positioned to draw fluid through system 530, so that the major flow through system 530 is drawn through and exhaust 535 and the fluid comprising the minor flow (after the particulates are deposited on the archival surface), exit through another port (not shown).

System 530 also includes a virtual impactor 532 adapted to separate the fluid into a major flow and a minor flow that includes particulates of a desired size range that are directed onto an archival surface 534. Virtual impactor 532 can one of the virtual impactors described above, although it is also contemplated that other designs of virtual impactors might also be used. A fluid is forced into virtual impactor 532 by fan 533, and as described above that fluid is separated into both a major flow and a minor flow. The major flow is directed to exhaust 535, while the minor flow is directed to an archival surface 534.

Archival surface 534 can incorporate any of the coating discussed above, or no coating. The configuration of archival surface 534 can include, but is not limited to, a plate, a disk, or an elongate tape. Preferably, archival surface 534 can be readily removed and replaced with a new archival surface either when the original archival surface is full, or particulates deposited on the archival surface require analysis. A vacuum source 546 is optionally in fluid communication with archival surface, also as described above, to assist in the deposition of the particulates thereon.

Preferably, archival surface 534 is coupled to a prime mover 536 that moves the archival surface relative to virtual impactor 532 over time, so that particulates collected at different times are deposited on different portions of archival surface 534. It should be noted that prime mover 536 can instead optionally move virtual impactor 532, instead of, or in addition to, moving archival surface 534.

With respect to embodiments in which prime mover 536 is drivingly coupled to archival surface 534, several different types of motion are contemplated. If archival surface 534 is a disk, prime mover 536 will likely be used to rotate the disk. If archival surface 534 is an elongate tape, then prime mover 536 will likely be used to cause one or both of a take-up wheel or a drive wheel (not shown) to be moved, to cause a corresponding movement in the elongate tape. Note that archival surface 534 is a consumable component, which when full, will be replaced with a fresh archival surface.

Prime mover 536 is controllably coupled to a control 538. The purpose of control 536 is to control the movement of prime mover 536 to achieve the desired movement at least one of virtual impactor 532 and archival surface 534. It is anticipated that control 538 can be one of a computing device, an application specific integrated circuit (ASIC), a hard wired logic circuit, or a simple timing circuit. In at least one embodiment, software is executed to control the operation of the device, and the control includes memory and a microprocessor. This software preferably includes a program that determines the positioning of the archival surface relative to the minor flow. The software may also include a program that controls the schedule for taking environmental samples at predetermined times, thereby producing a spot on the surface at specific spaced-apart times. In addition, the invention may execute logic that modifies the sampling schedule in accordance with algorithms that are responsive to onboard sensors 540. Finally, the software can monitor the particulate collection, generating a log of the actual time when each samples is taken in association with the disposition of the spot deposited on an archival surface at that time. This log facilitates correlating a specific sample (i.e., a specific spot) with a particular moment in time at which the spot was deposited. Control 538 is shown as being controllably coupled to fan 533. According to one sampling protocol, fan 533 will operate continuously. According to another sampling protocol, fan 533 will operate for a predefined period of time while a spot is being deposited on the archival surface, and then will be de-energized by the control. It is preferable that the flow of fluid into the system be interrupted between the deposition of samples that deposited as spots, and when the archival surface is being replaced.

Empirical tests of a prototype device, functionally similar to system 530, and employing a polymeric tape as an archival surface, has confirmed the ability of a virtual impactor to deposit spots of particulates on a movable archival surface.

As noted above, in some embodiments, system 530 may beneficially include sensors 540, which communicate with control 538 to cause a sample to be collected in response to an event that is detected by the sensors (i.e., one or more sensors). For example, an archival system may be mounted in a smokestack of a manufacturing facility, to generate an archival record of emissions from the smokestack. Such a system might be equipped with a carbon monoxide monitor, and when levels of carbon monoxide achieve a predetermined level, controller 538 (based on sensor data from sensors 540) can be programmed to initiate a sampling event, to deposit particulates on the archival surface for later analysis in response to the sensor readings. Such sensors can be used to measure relevant environmental factors that include, but are not limited to, pressure, humidity, temperature, particulate count, and presence of a particular target bio-molecule (such as particular cell types, pathogens, and toxins). Based on the detection of a specific environmental factor by such a sensor, or in accord with a sampling protocol programmed into control 538, one or more of the following functions can be executed by control 538:

Generate a record of the environmental conditions at the time of spotting

Control the operation of any system components whose performance depends on a measured environmental parameters Manipulate a programmed sampling protocol based on measured environmental factors Produce an alert signal (by means such as radio transmission or hard wired signal transmission) to notify an operator of an important change in the environmental conditions (as determined by programmed control parameters).

Figure 18:
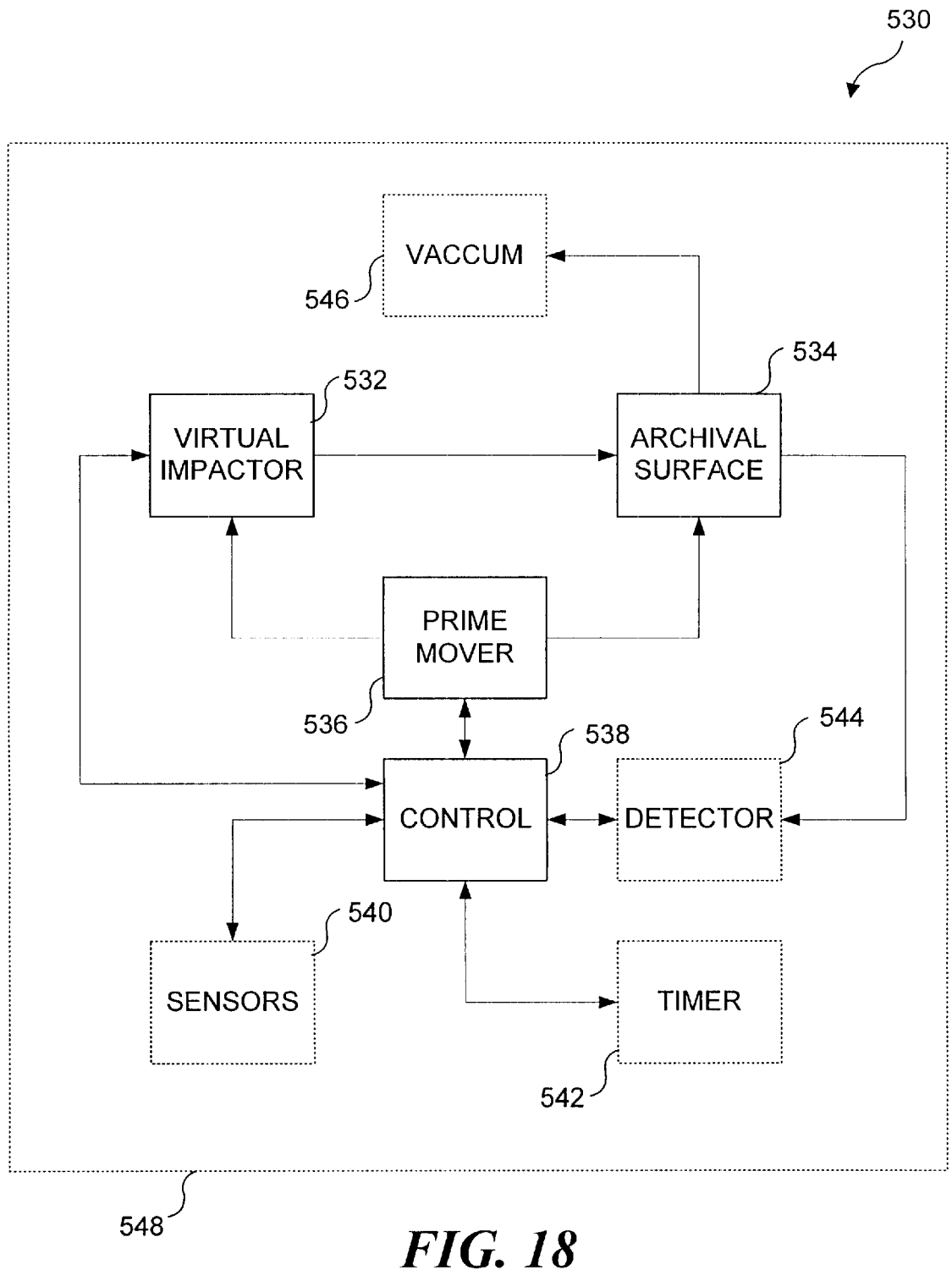
FIG. 18 is a block diagram of the components of an exemplary archival spot collection system.

Referring once again to FIG. 18, a timer 542 is optionally included to provide a timing signal to control 538. Depending on the type of computing device (or logical circuit) employed for control 538, timer 542 may not be required. Many computing devices do not require a separate timer, and in its simplest form, control 538 may itself comprise a timer or timing integrated circuit.

One or more optional detectors 544 can be included, to analyze particulates deposited on the archival surface. It is expected however, that the archival surface will most often be removed from the system before any of the particulates (i.e. spots) are analyzed. By using a separate detector, the cost of system 530 can be reduced, as detectors are often sophisticated and expensive. Furthermore, many detection methods require particulates comprising the spots to be removed from the archival surface before being analyzed. If detector 544 requires the particulates comprising the spots to be removed from the archival surface prior to analysis, a particulate removal system (generally a liquid rinse directed at a specific spot) must also be incorporated. Particulates comprising the spots can also be removed by scraping, and other means.

Preferably system 530 will often be used in a fixed (permanent) location to monitor a specific geographical location over a long period of time. Spent archival surfaces will be removed for storage and or analysis, and new archival surfaces will be inserted in system 530. It is anticipated that system 530 can also be used as a survey instrument that is moved from one location to another, to sample different geographic regions. Such a survey instrument can be used to obtain samples (spots) from many locations within a region on a single archival surface. This feature has utility in determining the source of a particular contaminant and monitoring a number of locations when the spots on the archival surface are subsequently analyzed.

While not specifically shown, it is further contemplated that system 530 can beneficially incorporate the ability to communicate with a control system at a remote location, to send and receive control signals and other data.

In many applications, it will be important that the system be able to sample a large volume of air ($\geq 300$ 1 pm), but it is also desirable that the sample collected be deposited in a small area (i.e., as spots ~1 mm in diameter). To achieve these goals, it will be important to achieve the separation of particulates from a large air volume and their concentration in a relatively smaller air volume (i.e., the minor flow). In such applications, it is contemplated that two in-line stages of virtual impaction may be preferable. In the first stage, 90% of the inlet fluid is discarded, and the remaining 10% of the fluid (1$^{st}$ stage minor flow) contains the desired particles. This 1$^{st}$ stage minor flow then enters a second virtual impactor stage with 90% of fluid that enters the second stage being exhausted. Therefore, the two stages have the combined effect of concentrating the outlet minor fluid volume to 1/100$^{th}$ of the initial inlet flow volume. This relatively small minor flow should then be in the correct range for depositing the concentration of particulates as spots onto a small surface area. Preferably, the spot density on the surface will be as high as possible, without cross-sample contamination occurring, in order to minimize the required area of the archival surface.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for separating and collecting particulates entrained in a flow of fluid, said apparatus comprising:
    (a) a virtual impactor capable of separating a fluid stream into a major flow and a minor flow, the major flow including a minor portion of particulates that are above a predetermined size and the minor flow including a major portion of the particulates that are above the predetermined size, said virtual impactor including a minor flow outlet through which the minor flow exits the virtual impactor;
    (b) an archival surface disposed adjacent to said virtual impactor, such that the minor flow of fluid moving through said minor flow outlet is directed toward said archival surface; said archival surface comprising a coating disposed on the archival surface that enhances a collection and retention of the particulates on the archival surface, wherein said coating comprises at least one of:
        (i) a material characterized by its ability to retain particulates impacting thereon when dry, and having a relatively low coefficient of friction when wetted, so that the particulates that have impacted on the archival surface and been retained thereon are readily washed from said surface with a liquid, said material being further characterized by being hydrophilic when dry, and hydrophobic when wetted;
        (ii) a material that attracts substantially only biologic particulates of a specific desired type, for efficiently separating said particulates from the minor flow of fluid, said coating binding with the particulates of the specific desired type to retain them on the archival surface; and
        (iii) a material that changes state while being retained on the impact collection surface, a first state of the material characterized by its ability to retain the particulates that impact thereon, separating the particulates from the minor flow of fluid, and a second state of the material characterized by its ability to readily release the particulates separated from the minor flow of fluid; and
    (c) a prime mover drivingly coupled to one of said virtual impactor and said archival surface, causing a relative position of said virtual impactor and said archival surface to be selectively changed over time, so that the minor flow of fluid moving through said minor flow outlet is directed toward a different portion of said archival surface over time.

2. The apparatus of claim 1, wherein said material characterized by its ability to retain particulates impacting thereon when dry, and having a relatively low coefficient of friction when wetted comprises at least one of parylene and tetraethylene glycol dimethyl ether.

3. The apparatus of claim 1, wherein said material that attracts substantially only biologic particulates of a specific desired type comprises an antibody selected so that substantially only particulates having a corresponding antigen are retained by the coating.

4. A method for separating a fluid flow in which particulates are entrained into a major flow that includes a minor portion of particulates above a predetermined size and a minor flow that includes a major portion of the particulates above the predetermined size, and for depositing and collecting those particulates entrained in said minor flow, comprising the steps of:
    (a) providing an archival surface having at least one surface enhancement that enhances a collection and retention of the particulates on the archival surface, said at least one surface enhancement comprising at least one of an indentation and a coating, wherein said coating comprises one of:
        (i) a material characterized by its ability to retain particulates impacting thereon when dry, and having a relatively low coefficient of friction when wetted, so that the particulates that have impacted on the archival surface and been retained thereon are readily washed from said surface with a liquid, said material being further characterized by being hydrophilic when dry, and hydrophobic when wetted;
        (ii) a material that attracts substantially only biological particulates of a specific desired type, for efficiently separating said biological particulates from the minor flow of fluid, said coating binding with the biological particulates of the specific desired type to retain them on the archival surface;
        (iii) a material that changes state while being retained on the impact collection surface, a first state of the material characterized by its ability to retain the particulates that impact thereon, separating the particulates from the minor flow of fluid, and a second state of the material characterized by its ability to readily release the particulates separated from the minor flow of fluid; and
        (iv) a material that comprises a plurality of openings into which particulates are directed;
    (b) directing the fluid flow into a virtual impactor, for separating the fluid flow into the major flow and the minor flow;
    (c) directing the minor flow onto the archival surface, such that particulates entrained in the minor flow are deposited on the archival surface; and
    (d) changing a relative position between the virtual impactor and the archival surface over time, such that particulates deposited on the archival surface before said relative position is changed are disposed on a different portion of said archival surface than particulates deposited after said relative position is changed.

5. The method of claim 4, wherein the step of directing the fluid flow into a virtual impactor capable of separating the fluid flow into the major flow and the minor flow comprises the steps of directing the fluid flow into a first virtual impactor that produces a first minor flow, and then directing the first minor flow into a second virtual impactor that produces a second minor flow, such that the second minor flow contains a substantially greater concentration of particulates than the first minor flow.

6. The method of claim 4, wherein the step of directing the fluid flow into a virtual impactor comprises the step of directing the fluid flow into a plurality of virtual impactors disposed in parallel, such that each different virtual impactor produces a distinct and separate minor flow, and each distinct and separate minor flow is directed toward a different portion of the archival surface, a cut size of each virtual impactor being substantially the same.

7. The method of claim 4, wherein if the surface enhancement comprises the indentation, further comprising the step of directing the minor flow toward the indentation to retain and collect the particulates in the minor flow within the indentation.

8. The method of claim 4, if said at least one surface enhancement comprises the coating, further comprising the step of directing the minor flow toward the coating.

9. The method of claim 4, wherein the step of changing a relative position between the virtual impactor and the archival surface over time comprises the step of moving the archival surface.

10. The method of claim 4, wherein the step of changing a relative position between the virtual impactor and the archival surface over time comprises the step of moving the virtual impactor.

11. The method of claim 4, wherein the step of changing a relative position between the virtual impactor and the archival surface over time comprises the step of continually changing the relative position to deposit the particulates on the archival surface in a streak.

12. The method of claim 4, wherein the step of changing a relative position between the virtual impactor and the archival surface over time comprises the step of waiting a defined period of time before changing the relative position, such that the particulates are deposited on the archival surface in a plurality of spaced-apart spots.

13. The method of claim 4, further comprising the step of detecting an environmental condition, wherein the step of changing the relative position between the virtual impactor and the archival surface over time comprises the step of changing the relative position in response to the environmental condition that is detected.

14. The method of claim 4, further comprising the step of applying a vacuum to a side of the archival surface opposite a side toward which the minor flow is directed, such that the vacuum draws the minor flow through the porous archival surface, thereby enhancing the deposition of the particulates on the archival surface.

15. The method of claim 4, further comprising the steps of providing a vacuum applied to an enclosed region adjacent to the archival surface, to enhance the deposition of the particulates on the archival surface.

16. Apparatus for separating and collecting particulates entrained in a flow of fluid, said apparatus comprising:
(a) a virtual impactor capable of separating a fluid stream into a major flow and a minor flow, the major flow including a minor portion of particulates that are above a predetermined size and the minor flow including a major portion of the particulates that are above the predetermined size, said virtual impactor including a minor flow outlet through which the minor flow exits the virtual impactor;
(b) an archival surface disposed adjacent to said virtual impactor, such that the minor flow of fluid moving through said minor flow outlet is directed toward said archival surface; said archival surface comprising a coating disposed on the archival surface that enhances a collection and retention of the particulates on the archival surface, wherein said coating comprises at least one of:
 (i) parylene;
 (ii) tetraethylene glycol dimethyl ether; and
 (iii) an antibody selected so that substantially only particulates having a corresponding antigen are retained by the coating; and
(c) a prime mover drivingly coupled to one of said virtual impactor and said archival surface, causing a relative position of said virtual impactor and said archival surface to be selectively changed over time, so that the minor flow of fluid moving through said minor flow outlet is directed toward a different portion of said archival surface over time.

17. A method for separating a fluid flow in which particulates are entrained into a major flow that includes a minor portion of particulates above a predetermined size and a minor flow that includes a major portion of the particulates above the predetermined size, and for depositing and collecting those particulates entrained in said minor flow, comprising the steps of:
(a) providing an archival surface having at least one surface enhancement that enhances a collection and retention of the particulates on the archival surface, said at least one surface enhancement comprising at least one of an indentation and a coating, wherein said coating comprises one of:
 (i) a material characterized by its ability to retain particulates impacting thereon when dry, and having a relatively low coefficient of friction when wetted, so that the particulates that have impacted on the archival surface and been retained thereon are readily washed from said surface with a liquid, said material being further characterized by being hydrophilic when dry, and hydrophobic when wetted;
 (ii) a material that attracts substantially only biologic particulates of a specific desired type, for efficiently separating said particulates from the minor flow of fluid, said coating binding with the particulates of the specific desired type to retain them on the archival surface; and
 (iii) a material that changes state while being retained on the impact collection surface, a first state of the material characterized by its ability to retain the particulates that impact thereon, separating the particulates from the minor flow of fluid, and a second state of the material characterized by its ability to readily release the particulates separated from the minor flow of fluid;
 (iv) a matreial facilitating survival of biological organisms, so that particulates comprising biological organisms that are deposited and retained on said archival surface are preserved in a living state for an extened period of time; and
 (v) a material that comprises a plurality of openings into which particulates are directed;
(b) directing the fluid into a virtual impactor, for separating the fluid flow into the major flow and the minor flow;
(c) directing the minor flow onto the archival surface, such that particulates entrained in the minor flow are deposited on the archival surface; and
(d) changing a relative position between the virtual impactor and the archival (d) changing a relative position between the virtual impactor and the archival surface over time by causing relative movement between the virtual impactor and the archival surface, such that particulates deposited on the archival surface before said relative position is changed are disposed on a different portion of said archival surface than particulates deposited after said relative position is changed.

* * * * *

UNITED STATES PATENT AND TRADEMARK OFFICE
CERTIFICATE OF CORRECTION

PATENT NO. : 6,695,146 B2
DATED : February 24, 2004
INVENTOR(S) : Charles Call et al.

It is certified that error appears in the above-identified patent and that said Letters Patent is hereby corrected as shown below:

Column 1,
Line 3, "APPLICATION" should read -- APPLICATIONS --

Column 28,
Line 40, "biologic" should read -- biological --
Line 42, after "said" insert -- biological --
Line 43, after "the" (first occurrence) insert -- biological --
Line 54, "matreial" should rad -- material --
Line 58, "extened" should read -- extended --
Line 61, after "fluid" insert -- flow --
Lines 67-68, after "; and" delete "((d) changing a relative position between the virtual impactor and the archival"

Signed and Sealed this

Twenty-eighth Day of September, 2004

JON W. DUDAS
*Director of the United States Patent and Trademark Office*